US011974880B2

(12) United States Patent
Jin et al.

(10) Patent No.: US 11,974,880 B2
(45) Date of Patent: May 7, 2024

(54) ULTRASOUND DIAGNOSIS APPARATUS CONNECTED TO WIRELESS ULTRASOUND PROBES AND METHOD OF OPERATING THE SAME

(71) Applicant: SAMSUNG MEDISON CO., LTD., Gangwon-do (KR)

(72) Inventors: Gil-ju Jin, Gangwon-do (KR); Yu-ri Kim, Gangwon-do (KR); Mi-jeoung Ahn, Gangwon-do (KR); Jae-moon Jo, Gangwon-do (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 0 days.

(21) Appl. No.: 18/132,102

(22) Filed: Apr. 7, 2023

(65) Prior Publication Data
US 2023/0240652 A1 Aug. 3, 2023

Related U.S. Application Data

(63) Continuation of application No. 17/339,261, filed on Jun. 4, 2021, now Pat. No. 11,647,986, which is a
(Continued)

(30) Foreign Application Priority Data

Dec. 27, 2017 (KR) ........................ 10-2017-0181453

(51) Int. Cl.
*A61B 8/00* (2006.01)
*A61B 8/08* (2006.01)
(52) U.S. Cl.
CPC ............ *A61B 8/4472* (2013.01); *A61B 8/565* (2013.01); *A61B 8/4405* (2013.01); *A61B 8/4477* (2013.01);
(Continued)

(58) Field of Classification Search
CPC ............................ A61B 8/4472; A61B 8/565
See application file for complete search history.

(56) References Cited

U.S. PATENT DOCUMENTS 8,721,551 B2   5/2014   Tanabe
9,218,452 B2   12/2015  Varna et al.
(Continued)

FOREIGN PATENT DOCUMENTS

CN   203555769 U   4/2014
CN   106377280 A   2/2017
(Continued)

OTHER PUBLICATIONS

Communication under Rule 71(3) EPC issued in corresponding European Application No. 18 849 186.4 dated Jun. 16, 2023.
(Continued)

*Primary Examiner* — Joseph M Santos Rodriguez
(74) *Attorney, Agent, or Firm* — Morgan, Lewis & Bockius LLP

(57) ABSTRACT

Provided are an ultrasound diagnosis apparatus connected to wireless ultrasound probes and a method of operating the ultrasound diagnosis apparatus. The ultrasound diagnosis apparatus includes: a communicator connected with a plurality of different wireless probes through a wireless communication method by receiving pairing reception signals from the plurality of wireless ultrasound probes; a controller configured to control the communicator to wirelessly connect the ultrasound diagnosis apparatus with the plurality of wireless ultrasound probes and to wirelessly receive status information regarding the connected plurality of wireless ultrasound probes; and a display configured to display a user interface (UI) indicating the received status information regarding the plurality of wireless ultrasound probes.

20 Claims, 12 Drawing Sheets

Related U.S. Application Data continuation of application No. 15/871,212, filed on Jan. 15, 2018, now Pat. No. 11,051,787.

(60) Provisional application No. 62/550,054, filed on Aug. 25, 2017.

(52) U.S. Cl.
CPC ............... *A61B 8/463* (2013.01); *A61B 8/464* (2013.01); *A61B 8/466* (2013.01); *A61B 8/467* (2013.01); *A61B 8/5207* (2013.01)

(56) References Cited

U.S. PATENT DOCUMENTS

| | | | |
|---|---|---|---|
| 9,504,445 | B2 | 11/2016 | Holl et al. |
| 9,610,065 | B2 | 4/2017 | Kim et al. |
| 9,622,718 | B2 | 4/2017 | Watanabe |
| 2010/0168576 | A1 | 7/2010 | Poland et al. |
| 2010/0191121 | A1 | 7/2010 | Satoh et al. |
| 2011/0105904 | A1* | 5/2011 | Watanabe ............... A61B 8/56 600/443 |
| 2012/0071762 | A1 | 3/2012 | Sato |
| 2012/0108960 | A1 | 5/2012 | Halmann et al. |
| 2014/0107487 | A1* | 4/2014 | Kim .................... A61B 8/4438 600/459 |
| 2014/0323869 | A1* | 10/2014 | Jin ..................... A61B 8/4472 600/459 |

FOREIGN PATENT DOCUMENTS

| | | |
|---|---|---|
| JP | 2000-325350 A | 11/2000 |
| JP | 2007-275087 A | 10/2007 |
| JP | 2012-90712 A | 5/2012 |
| JP | 2012-139491 A | 7/2012 |
| JP | 2016-220739 A | 12/2016 |
| JP | 2010-528696 A | 8/2019 |
| KR | 10-2010-0057341 A | 5/2010 |
| KR | 10-2012-0127072 A | 11/2012 |
| KR | 10-2014-0129776 A | 11/2014 |
| KR | 10-1733731 B1 | 5/2017 |
| WO | 2010/122791 A1 | 10/2010 |
| WO | 2017/009735 A1 | 1/2017 |

OTHER PUBLICATIONS

Office Action issued in corresponding Korean Patent Application No. 10-2017-0181453 dated Jun. 21, 2023, with English translation.
International Search Report dated Aug. 14, 2018 issued in International Patent Application No. PCT/KR2018/004238 (with English translation).
U.S. Office Action dated Apr. 8, 2020 issued in U.S. Appl. No. 15/871,212.
Extended European Search Report dated Apr. 28, 2020 issued in European Patent Application No. 18849186.4.
U.S. Final Office Action dated Oct. 16, 2020 issued in U.S. Appl. No. 15/871,212.
Korean Office Action dated Dec. 16, 2022 issued in Korean Patent Application No. 10-2017-0181453 (with English translation).
U.S. Notice of Allowance dated Jan. 10, 2023 issued in U.S. Appl. No. 17/339,261.
Korean Notice of Allowance dated Nov. 14, 2023 issued in Korean Patent Application No. 10-2017-0181453 (with English translation).
European Invitation dated Dec. 1, 2023 issued in European Patent Application No. 23 203 353.0.
Chinese Office Action dated Jan. 19, 2024 issued in Chinese Patent Application No. 201880051615.3 (with English translation).
Extended European Search Report dated Mar. 6, 2024 issued in European Patent Application No. 23203353.0.
Korean Office Action dated Mar. 12, 2024 issued in Korean Patent Application No. 10-2024-0021205 (with English translation).

* cited by examiner

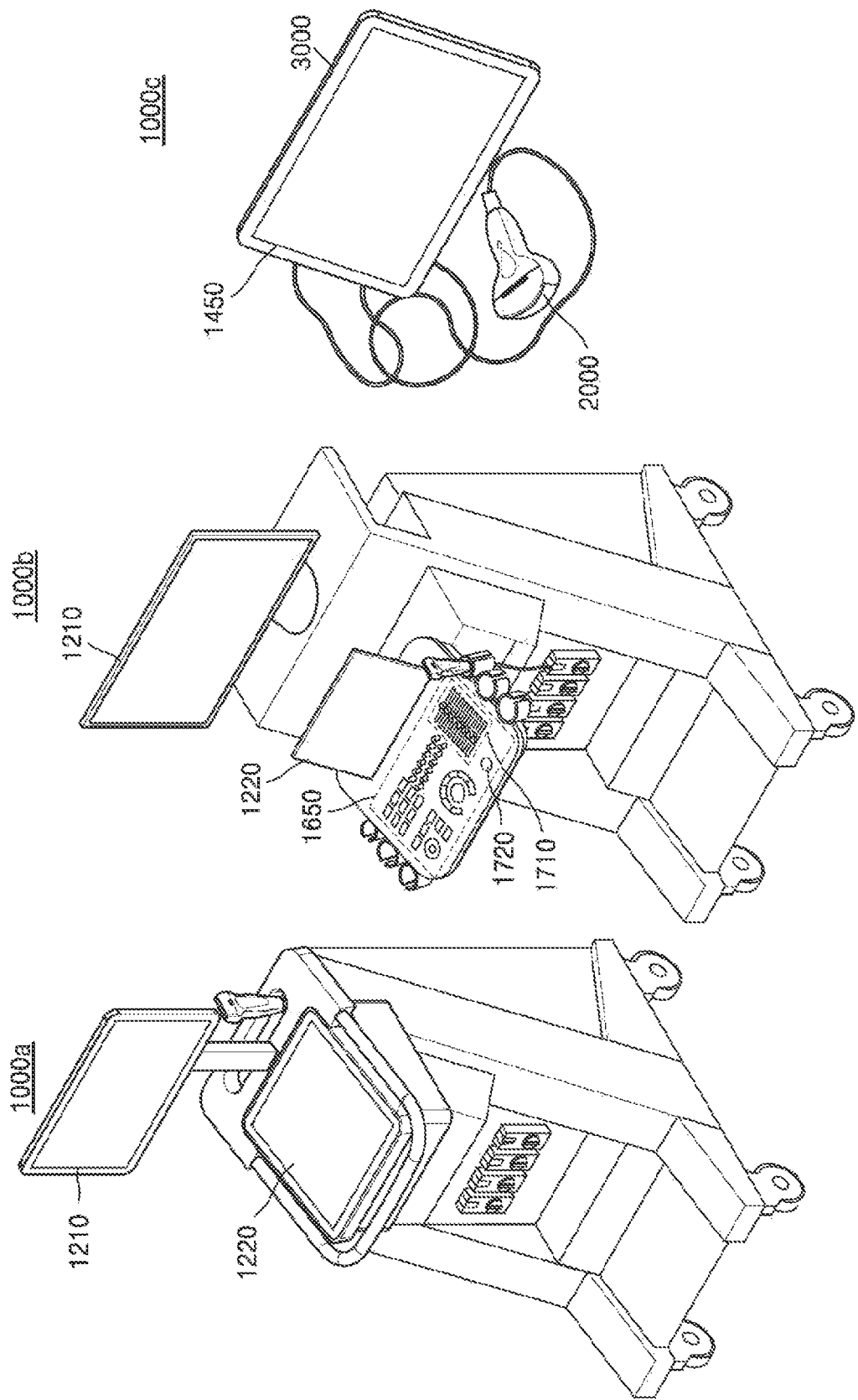

ULTRASOUND DIAGNOSIS APPARATUS CONNECTED TO WIRELESS ULTRASOUND PROBES AND METHOD OF OPERATING THE SAME

CROSS-REFERENCE TO RELATED APPLICATIONS

This application is a Continuation Application of U.S. patent application Ser. No. 17/339,261, filed on Jun. 4, 2021, which is a Continuation Application of U.S. patent application Ser. No. 15/871,212, filed on Jan. 15, 2018, now U.S. Pat. No. 11,051,787, issued on Jul. 6, 2021, which claims the benefit of U.S. Provisional Application No. 62/550,054, filed on Aug. 25, 2017, in the U.S. Patent Office and Korean Patent Application No. 10-2017-0181453, filed on Dec. 27, 2017, in the Korean Intellectual Property Office, the disclosures of which are incorporated herein in their entirety by reference.

BACKGROUND

1. Field

The present disclosure relates to ultrasound diagnosis apparatuses connected to wireless ultrasound probes and methods of operating the ultrasound diagnosis apparatuses, and more particularly, to ultrasound diagnosis apparatuses paired with a plurality of wireless ultrasound probes and operation methods for displaying status information regarding the paired plurality of wireless ultrasound probes on a display of the ultrasound diagnosis apparatus.

2. Description of Related Art

Ultrasound systems transmit ultrasound signals generated by transducers of an ultrasound probe to an internal part of an object and receive information about echo signals reflected therefrom, thereby obtaining an image of the internal part of the object. In particular, ultrasound systems are used for medical purposes including observation of an internal area of an object, detection of foreign substances, diagnosis of damage to the object, and imaging of characteristics.

Wireless ultrasound probes connected to an ultrasound diagnosis apparatus by using wireless communication are nowadays being developed in order to improve the operability of an ultrasound probe by removing a communication cable for transmitting and receiving ultrasound image data between the ultrasound probe and the ultrasound diagnosis apparatus and eliminating the inconvenience caused by the communication cable. However, at the present time, an ultrasound diagnosis apparatus including a wireless ultrasound probe may contain only one wireless ultrasound probe, and only one wireless ultrasound probe may be connected to the ultrasound diagnosis apparatus. Furthermore, even when an ultrasound diagnosis apparatus includes a plurality of wireless ultrasound probes, only one of the plurality of wireless ultrasound probes may be paired to the ultrasound diagnosis apparatus. Thus, in the case that a user desires to use a wireless ultrasound probe other than a wireless ultrasound probe currently paired to the ultrasound diagnosis apparatus, the user suffers the inconvenience of having to disconnect the paired wireless ultrasound probe and pair the desired wireless ultrasound probe again.

SUMMARY

Provided are ultrasound diagnosis apparatuses simultaneously connected with a plurality of wireless ultrasound probes and configured to display a user interface (UI) indicating identification (ID) information regarding the plurality of wireless ultrasound probes connected thereto. The ultrasound diagnosis apparatuses may display UIs indicating status information regarding the plurality of wireless ultrasound probes paired using a wireless communication method.

Additional aspects will be set forth in part in the description which follows and, in part, will be apparent from the description, or may be learned by practice of the presented embodiments.

In accordance with an aspect of the present disclosure, an ultrasound diagnosis apparatus includes: a communicator connected with a plurality of different wireless probes through a wireless communication method by receiving pairing reception signals from the plurality of wireless ultrasound probes; a controller configured to control the communicator to wirelessly connect the ultrasound diagnosis apparatus with the plurality of wireless ultrasound probes and to wirelessly receive status information regarding the connected plurality of wireless ultrasound probes; and a display configured to display a user interface (UI) indicating the received status information regarding the plurality of wireless ultrasound probes.

For example, the communicator may include a plurality of communication modules paired one-to-one with the plurality of wireless ultrasound probes and configured to respectively transmit or receive ultrasound image data to or from the plurality of wireless ultrasound probes.

The communicator may be connected with the plurality of wireless ultrasound probes by using at least one of wireless communication methods including a Wireless Local Area Network (WLAN), Wireless Fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

The communicator may be configured to acquire insert information about a wireless ultrasound probe inserted into a holder of the ultrasound diagnosis apparatus, among the plurality of wireless ultrasound probes. The controller may be further configured to detect the wireless ultrasound probe inserted into the holder, based on the insert information, and the display may be further configured to display connection information regarding the wireless ultrasound probe detected among the plurality of wireless ultrasound probes.

The display may be further configured to display a UI indicating the status information including at least one of an identification (ID), a wireless communication frequency, a connection type, a supported application, a wireless communication method, a communication status, battery charging information, a remaining battery capacity, and a time left for use with respect to each of the plurality of wireless ultrasound probes.

The communicator may be configured to receive, from an activated wireless ultrasound probe, ultrasound raw data generated by the wireless ultrasound probe activated among the plurality of wireless ultrasound probes, and the display may be further configured to display a UI indicating a type of a wireless communication method used to transmit and receive ultrasound data to and from the activated wireless ultrasound probe.

The UI may include characters indicating identifications (IDs) of the plurality of wireless ultrasound probes and thumbnail images representing shapes thereof.

The ultrasound diagnosis apparatus may further include a user input interface configured to receive a user input of selecting one of the plurality of wireless ultrasound probes, and the communicator may be configured to transmit an activation signal for operating a first wireless ultrasound probe selected among the plurality of wireless ultrasound probes, based on the user input to transmit ultrasound signals to an object. The display may be further configured to display the first wireless ultrasound probe that has received the activation signal to be distinguished from the unselected ones of the plurality of wireless ultrasound probes.

The controller may be further configured to generate a beamformer control signal for controlling a beamformer included in each of the plurality of wireless ultrasound probes and control the communicator to transmit the generated beamformer control signal to the activated first wireless ultrasound probe.

The ultrasound diagnosis apparatus may further include a sound output unit configured to output a preset sound when the plurality of wireless ultrasound probes are connected wirelessly to the ultrasound diagnosis apparatus.

In accordance with another aspect of the present disclosure, a method of operating an ultrasound diagnosis apparatus includes: connecting a plurality of different wireless ultrasound probes with the ultrasound diagnosis apparatus by using a wireless communication method; receiving status information regarding the plurality of wireless ultrasound probes; and displaying a user interface (UI) indicating the received status information regarding the plurality of wireless ultrasound probes.

The connecting of the plurality of different wireless ultrasound probes with the ultrasound diagnosis apparatus may include: pairing wireless communication modules in the ultrasound diagnosis apparatus; one-to-one with the plurality of wireless ultrasound probes; and transmitting and receiving ultrasound image data respectively to and from the plurality of wireless ultrasound probes.

The connecting of the plurality of wireless ultrasound probes with the ultrasound diagnosis apparatus may include connecting the plurality of wireless ultrasound probes with the ultrasound diagnosis apparatus by using at least one of wireless communication methods including a Wireless Local Area Network (WLAN), wireless fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (Wi-Bro), World Interoperability for Microwave Access (WiMAX), Shared Wireless Access Protocol (SWAP), Wireless Gigabit Alliance (WiGig), and radio frequency (RF) communication.

The connecting of the plurality of wireless ultrasound probes with the ultrasound diagnosis apparatus may include: acquiring insert information about a wireless ultrasound probe inserted into a holder of the ultrasound diagnosis apparatus, among the plurality of wireless ultrasound probes; detecting the wireless ultrasound probe inserted into the holder, based on the insert information; and displaying pairing information regarding the wireless ultrasound probe detected among the plurality of wireless ultrasound probes.

The displaying of the UI may include displaying a UI indicating the status information including at least one of an identification (ID), a wireless communication frequency, a connection type, a supported application, a wireless communication method, a communication status, battery charging information, a remaining battery capacity, and a time left for use with respect to each of the plurality of wireless ultrasound probes.

The method may further include receiving, from an activated wireless ultrasound probe, ultrasound raw data generated by the wireless ultrasound probe activated among the plurality of wireless ultrasound probes, and the displaying of the UI may include displaying a UI indicating a type of a wireless communication method used to transmit and receive ultrasound data to and from the activated wireless ultrasound probe.

The displaying of the UI may include displaying characters indicating identifications (IDs) of the plurality of wireless ultrasound probes and thumbnail images representing shapes thereof.

The method may further include: receiving a user input of selecting one of the plurality of wireless ultrasound probes; transmitting an activation signal for operating a first wireless ultrasound probe selected among the plurality of wireless ultrasound probes based on the user input to transmit ultrasound signals to an object; and displaying the first wireless ultrasound probe that has received the activation signal to be distinguished from the unselected ones of the plurality of wireless ultrasound probes.

The method may further include generating a beamformer control signal for controlling a beamformer included in each of the plurality of wireless ultrasound probes and transmitting the generated beamformer control signal to the activated first wireless ultrasound probe.

The method may further include outputting a preset sound when the plurality of wireless ultrasound probes are connected wirelessly to the ultrasound diagnosis apparatus.

In accordance with another aspect of the present disclosure, a computer-readable recording medium having recorded thereon a computer program including instructions for performing operations of: connecting a plurality of different wireless ultrasound probes with an ultrasound diagnosis apparatus by using a wireless communication method; receiving status information regarding the plurality of wireless ultrasound probes; and displaying a user interface (UI) indicating the received status information regarding the plurality of wireless ultrasound probes.

BRIEF DESCRIPTION OF THE DRAWINGS

These and/or other aspects will become apparent and more readily appreciated from the following description of the embodiments, taken in conjunction with the accompanying drawings in which:

FIGS. 11A through 11C are diagrams illustrating ultrasound diagnosis apparatuses according to embodiments.

DETAILED DESCRIPTION

Figure 1:
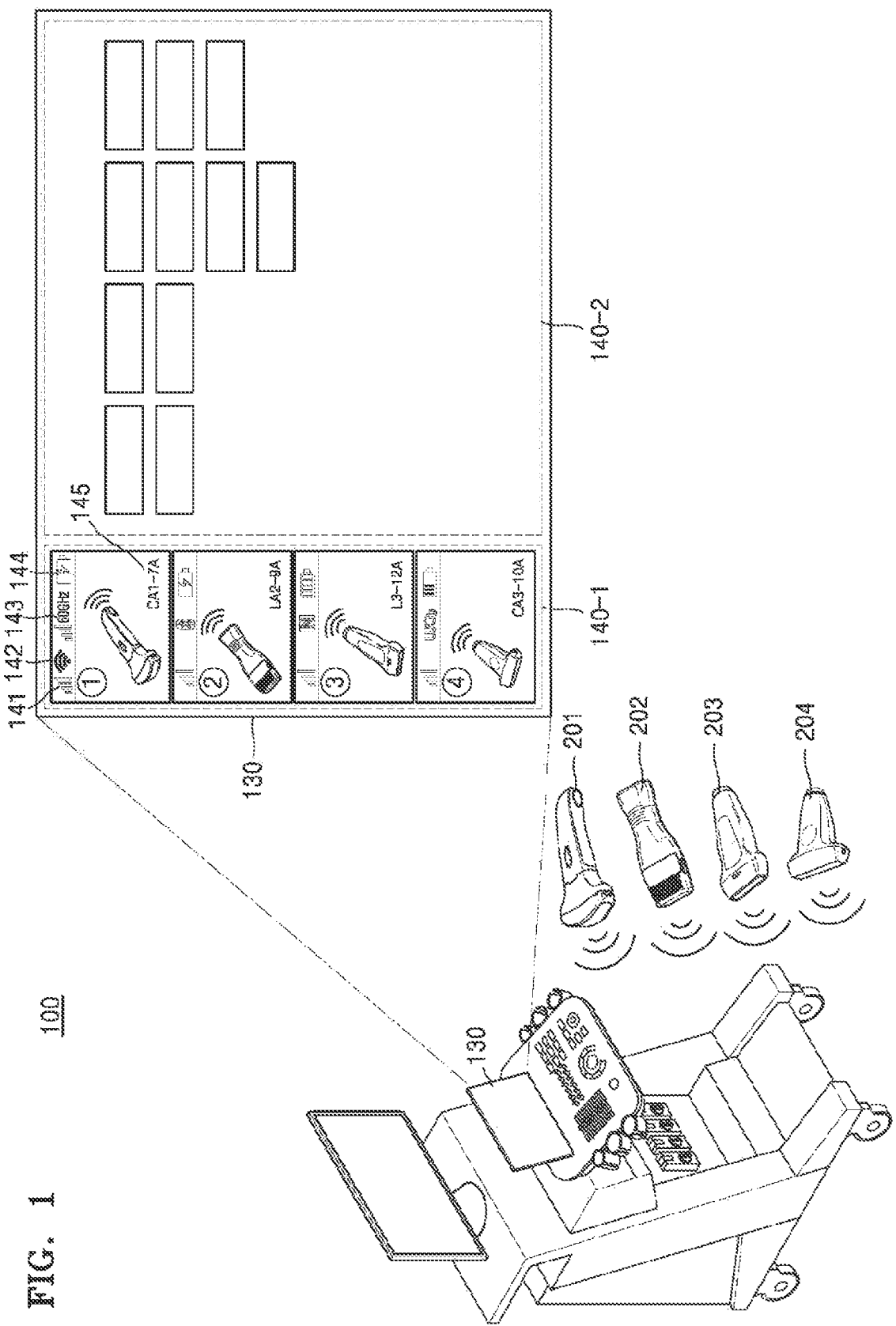
FIG. 1 is a conceptual diagram illustrating an example in which an ultrasound diagnosis apparatus is connected with a plurality of wireless ultrasound probes and displays status information regarding the plurality of wireless ultrasound probes connected thereto, according to an embodiment.

Advantages and features of one or more embodiments of the present invention and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present invention will only be defined by the appended claims.

Terms used herein will now be briefly described and then one or more embodiments of the present invention will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present invention means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

In the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, and a technician who repairs a medical apparatus.

Furthermore, in the present specification, the terms "first", "second", "1-1", etc. are only used to distinguish one component, element, object, image, pixel, or patch from another component, element, object, image, pixel, or patch. Thus, these terms are not limited to representing the order or priority among elements or components. Expressions such as "at least one of," when preceding a list of elements, modify the entire list of elements and do not modify the individual elements of the list.

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail so as not to obscure the embodiments with unnecessary detail.

FIG. 1 is a conceptual diagram illustrating an example in which an ultrasound diagnosis apparatus 100 is connected with a plurality of wireless ultrasound probes 201 through 204 and displays status information regarding the plurality of wireless ultrasound probes 201 through 204 connected thereto, according to an embodiment.

Referring to FIG. 1, the ultrasound diagnosis apparatus 100 may be connected with the wireless ultrasound probes 201 through 204 including first through fourth wireless ultrasound probes 201 through 204 by using a wireless communication method. Although FIG. 1 shows that the ultrasound diagnosis apparatus 100 is a cart type apparatus, it may be implemented as a portable type apparatus. Examples of portable ultrasound diagnosis apparatuses may include, but are not limited to, a picture archiving and communication system (PACS) viewer, a hand-carried cardiac ultrasound (HCU) device, a smartphone, a laptop computer, a personal digital assistant (PDA), and a tablet PC.

In an embodiment, the ultrasound diagnosis apparatus 100 may be an apparatus configured to generate an ultrasound image by processing ultrasound image data received from one of the wireless ultrasound probes 201 through 204 and display the generated image, or be an apparatus for implementing only an image display function without performing a separate image processing function.

Each of the wireless ultrasound probes 201 through 204 may transmit ultrasound signals to an object and receive echo signals reflected from the object to thereby produce reception signals. Each of the wireless ultrasound probes 201 through 204 may also perform image processing on the reception signals to thereby generate ultrasound image data and then transmit the generated ultrasound image data to the ultrasound diagnosis apparatus 100.

Although a total of four (4) wireless ultrasound probes 201 through 204 are shown throughout the specification including FIG. 1, this is merely an example, and the number of wireless ultrasound probes connected to the ultrasound diagnosis apparatus 100 is not limited to 4. The wireless ultrasound probes 201 through 204 may each be different types of probes having different functions, but embodiments are not limited thereto.

The wireless ultrasound probes 201 through 204 may be connected to the ultrasound diagnosis apparatus 100 by using a wireless communication method. In this case, "connected" may mean a state in which the ultrasound diagnosis apparatus 100 is paired to use at least one of the wireless ultrasound probes 201 through 204. Even when the ultrasound diagnosis apparatus 100 is connected with the wireless ultrasound probes 201 through 204, it does not mean that the ultrasound diagnosis apparatus 100 may use all of the wireless ultrasound probes 201 through 204 to transmit ultrasound signals to the object. "Pairing" is conceptually different from "activation", as will be described in more detail below with reference to FIGS. 8 and 9.

For example, the ultrasound diagnosis apparatus 100 may be connected wirelessly with the wireless ultrasound probes 201 through 204 by using local area wireless communication. For example, the ultrasound diagnosis apparatus 100 may be wirelessly paired with the wireless ultrasound probes 201 through 204 by using at least one of data communication methods including a Wireless Local Area Network (WLAN), Wireless Fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

According to an embodiment, the ultrasound diagnosis apparatus 100 may receive ultrasound raw data generated and digital-converted by a wireless ultrasound probe activated among the wireless ultrasound probe 201 through 204 by using a 60-GHz millimeter wave (mmWave) local area communication method. However, embodiments are not limited thereto, and the ultrasound diagnosis apparatus 100 may receive, through a WLAN or Wi-Fi, ultrasound image data that is used to construct an ultrasound image via an activated wireless ultrasound probe.

The ultrasound diagnosis apparatus 100 may display a user interface (UI) indicating status information regarding the wireless ultrasound probes 201 through 204 on a display 130. According to an embodiment, the display 130 may display a UI indicating status information including at least one of a wireless communication frequency, a connection type, a supported application, a wireless communication method, a communication status, battery charging information, a remaining battery capacity, and a time left for use with respect to each of the wireless ultrasound probes 201 through 204 connected wirelessly to the ultrasound diagnosis apparatus 100. For example, the display 130 may display a first UI 141 indicating a status of a wireless communication connection with the ultrasound diagnosis apparatus 100, a second UI 142 indicating a wireless pairing method for connecting to the ultrasound diagnosis apparatus 100, a third UI 143 indicating a communication method for transmitting or receiving ultrasound image data to or from the ultrasound diagnosis apparatus 100, and a fourth UI 144 indicating a remaining battery capacity or whether a battery is being charged. Furthermore, the display 130 may display a fifth UI 145 indicating ID information of each of the wireless ultrasound probes 201 through 204 connected wirelessly to the ultrasound diagnosis apparatus 100. UIs indicating status information will be described in more detail below with reference to FIGS. 6, 7A, and 7B.

The ultrasound diagnosis apparatus 100 may display on the display 130 connection states of the wireless ultrasound probes 201 through 204 that are connected wirelessly thereto, and embodiments are not limited thereto. According to an embodiment, the ultrasound diagnosis apparatus 100 may output a preset sound when wirelessly connected with the wireless ultrasound probes 201 through 204. Furthermore, in another embodiment, the ultrasound diagnosis apparatus 100 may output different sounds respectively according to ID information of the wireless ultrasound probes 201 through 204. For example, when the first and second wireless ultrasound probes 201 and 202 are respectively connected to the ultrasound diagnosis apparatus 100, the ultrasound diagnosis apparatus 100 may output first and second sounds, respectively.

A conventional ultrasound system including a wireless ultrasound probe includes only one wireless ultrasound probe, or even when the ultrasound system includes a plurality of wireless ultrasound probes, only one of the wireless ultrasound probes may be wirelessly paired thereto. Thus, when a user desires to use a wireless ultrasound probe other than a wireless ultrasound probe currently being paired, the user suffers the inconvenience of having to disconnect the paired wireless ultrasound probe and then pair the desired wireless ultrasound probe again.

On the other hand, the ultrasound diagnosis apparatus 100 according to the present embodiment may be wirelessly paired with the wireless ultrasound probes 201 through 204 simultaneously. Thus, when the user desires to use one of the wireless ultrasound probes 201 through 204, this configuration may allow the user to immediately use the desired wireless ultrasound probe without a separate additional pairing process, thereby increasing user convenience. Furthermore, the ultrasound diagnosis apparatus 100 may display a UI indicating status information including connection states of the wireless ultrasound probes 201 through 204 such that the user may easily identify a wireless connection state, a wireless communication method, and a remaining battery capacity of each of the wireless ultrasound probes 201 through 204.

Figure 2:
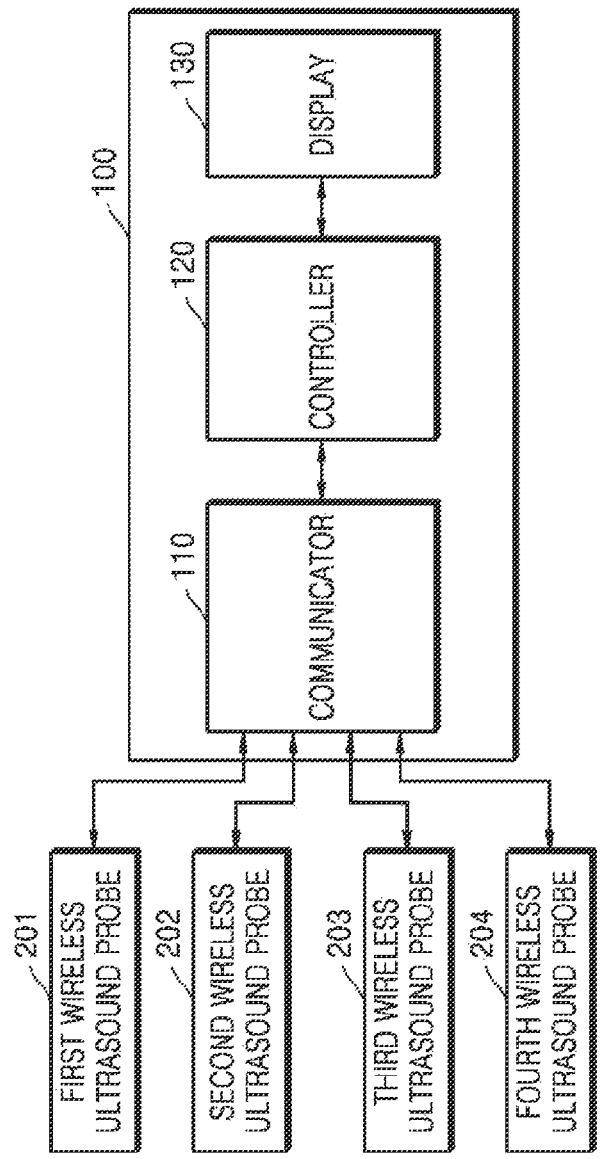
FIG. 2 is a block diagram of a configuration of an ultrasound system according to an embodiment.

FIG. 2 is a block diagram of a configuration of an ultrasound system according to an embodiment.

Referring to FIG. 2, the ultrasound system may include an ultrasound diagnosis apparatus 100 and a plurality of wireless ultrasound probes 201 through 204. The ultrasound diagnosis apparatus 100 may be implemented not only as a cart type apparatus but also as a portable type apparatus. Examples of portable ultrasound diagnosis apparatuses may include, but are not limited to, a PACS viewer, a HCU device, a smartphone, a laptop computer, a PDA, and a tablet PC.

In an embodiment, the ultrasound diagnosis apparatus 100 may be an apparatus configured to generate an ultrasound image by processing ultrasound image data received from one of the wireless ultrasound probes 201 through 204 and display the generated image, or be an apparatus for implementing only an image display function without performing a separate image processing function.

The ultrasound diagnosis apparatus 100 may include a communicator 110, a controller 120, and a display 130. The communicator 110 may be connected simultaneously with the wireless ultrasound probes 201 through 204 by using a wireless communication method. For example, the communicator 110 may simultaneously be paired wirelessly with the wireless ultrasound probes 201 through 204 by using at least one of wireless communication techniques including a WLAN, Wi-Fi, Bluetooth, Zigbee, WFD, IrDA, BLE, NFC, WiBro, WiMAX, SWAP, WiGig, and RF communication method.

According to an embodiment, the communicator 110 may include a wireless communication module for pairing with the wireless ultrasound probes 201 through 204 and a data communication module for receiving ultrasound raw data generated by a wireless ultrasound probe that is activated among the wireless ultrasound probes 201 through 204. The communicator 110 may include a 60-GHz mmWave data communication module and receive raw data via the 60-GHz mmWave data communication module. To acquire the raw data, a wireless ultrasound probe activated among the wireless ultrasound probes transmits ultrasound signals to the object, processes received ultrasound echo signals, and performs analog-to-digital conversion on the resulting signals. The wireless ultrasound probes 201 through 204 may be wirelessly paired to the ultrasound diagnosis apparatus 100 simultaneously, but only one of the wireless ultrasound probes 201 through 204 may be activated. Thus, the communicator 110 may include one 60-GHz mmWave data communication module for performing data communication with the one activated wireless ultrasound probe.

In another embodiment, the communicator 110 may not include the 60-GHz mmWave data communication module. When a wireless ultrasound probe that is activated among the wireless ultrasound probes 201 through 204 directly transmits to the display 130 image data that is used to construct an ultrasound image of the object, a relatively small amount of data may be transmitted compared to transmission of ultrasound raw data. In this case, the communicator 110 may include only a local area communication module for pairing.

According to an embodiment, the communicator 110 may wirelessly receive status information regarding the paired wireless ultrasound probes 201 through 204 respectively from the wireless ultrasound probes 201 through 204. The communicator 110 may periodically receive status information regarding each of the wireless ultrasound probes 201 through 204 to check a state thereof based on the status information. For example, the status information may include at least one of a wireless communication frequency, a connection type, a supported application, a wireless communication method, a communication status, battery charging information, a remaining battery capacity, and a time left for use with respect to each of the wireless ultrasound probes 201 through 204.

The controller 120 may control operations of the communicator 110 and the display 130. In detail, the controller 120 may control the communicator 110 to wirelessly pair the ultrasound diagnosis apparatus 100 with the wireless ultrasound probes 201 through 204 and wirelessly receive status information regarding the paired wireless ultrasound probes 201 through 204. Furthermore, the controller 120 may generate a UI indicating the status information regarding the wireless ultrasound probes 201 through 204, which are received via the communicator 110 and control the display 130 to display the generated UI.

For example, the controller 120 may be formed as a hardware module including at least one of a central processing unit (CPU), a microprocessor, a graphic processing unit, random-access memory (RAM), and read-only memory (ROM). In an embodiment, the controller 120 may be implemented as an application processor (AP). The controller 120 may also be implemented as a hardware component such as a field-programmable gate array (FPGA) or an application-specific integrated circuit (ASIC). However, embodiments are not limited thereto, and the controller 120 may include components such as software components, object-oriented software components, class components and task components, processes, functions, attributes, procedures, subroutines, segments of program code, drivers, firmware, micro codes, circuits, data, a database, data structures, tables, arrays, and variables.

The display 130 may display a UI indicating status information regarding each of the wireless ultrasound probes 201 through 204 wirelessly paired to the ultrasound diagnosis apparatus 100. According to an embodiment, the display 130 may display a graphical user interface (GUI) graphically representing at least one of a wireless communication frequency, a connection type, an executable application, a wireless communication method, a communication status, battery charging information, a remaining battery capacity, and a time left for use with respect to each of the wireless ultrasound probes 201 through 204. In an embodiment, the display 130 may display a GUI indicating a data communication method for receiving ultrasound raw data or image data acquired from imaging from a wireless ultrasound probe activated among the wireless ultrasound probes 201 through 204.

Furthermore, the display 130 may display characters respectively indicating ID information of the wireless ultrasound probes 201 through 204 and thumbnail images graphically representing shapes of the wireless ultrasound probes 201 through 204.

The display 130 may be constructed by a physical device including at least one of a cathode ray tube (CRT) display, a liquid crystal display (LCD), a plasma display panel (PDP), an organic light-emitting diode (OLED) display, a field-emission display (FED), an LED display, a vacuum fluorescent display (VFD), a digital light processing (DLP) display, a flat panel display, a three-dimensional (3D) display, and a transparent display, and embodiments are not limited thereto. According to an embodiment, the display 130 may be formed as a touch screen including a touch interface. When the display 130 is formed as a touch screen, the display 130 may be integrated with a touch pad to receive a user touch input.

Each of the wireless ultrasound probes 201 through 204 may transmit ultrasound signals to an object and receive echo signals reflected from the object to produce reception signals. Each of the wireless ultrasound probes 201 through 204 may also perform image processing on the reception signals to thereby generate ultrasound image data. The wireless ultrasound probes 201 through 204 may be wirelessly connected to the ultrasound diagnosis apparatus 100 simultaneously via the communicator 110. According to an embodiment, the wireless ultrasound probes 201 through 204 may transmit generated ultrasound image data wirelessly to the ultrasound diagnosis apparatus 100 via the communicator 110.

Although not shown in FIG. 2, the ultrasound diagnosis apparatus 100 may further include a sound output unit. The sound output unit may output a preset sound when the ultrasound diagnosis apparatus 100 is connected wirelessly with the wireless ultrasound probes 201 through 204. According to an embodiment, the sound output unit may output different sounds respectively according to ID information of the wireless ultrasound probes 201 through 204. For example, when the first and second wireless ultrasound probes 201 and 202 are respectively connected to the ultrasound diagnosis apparatus 100, the sound output unit may output first and second sounds, respectively.

Figure 3:
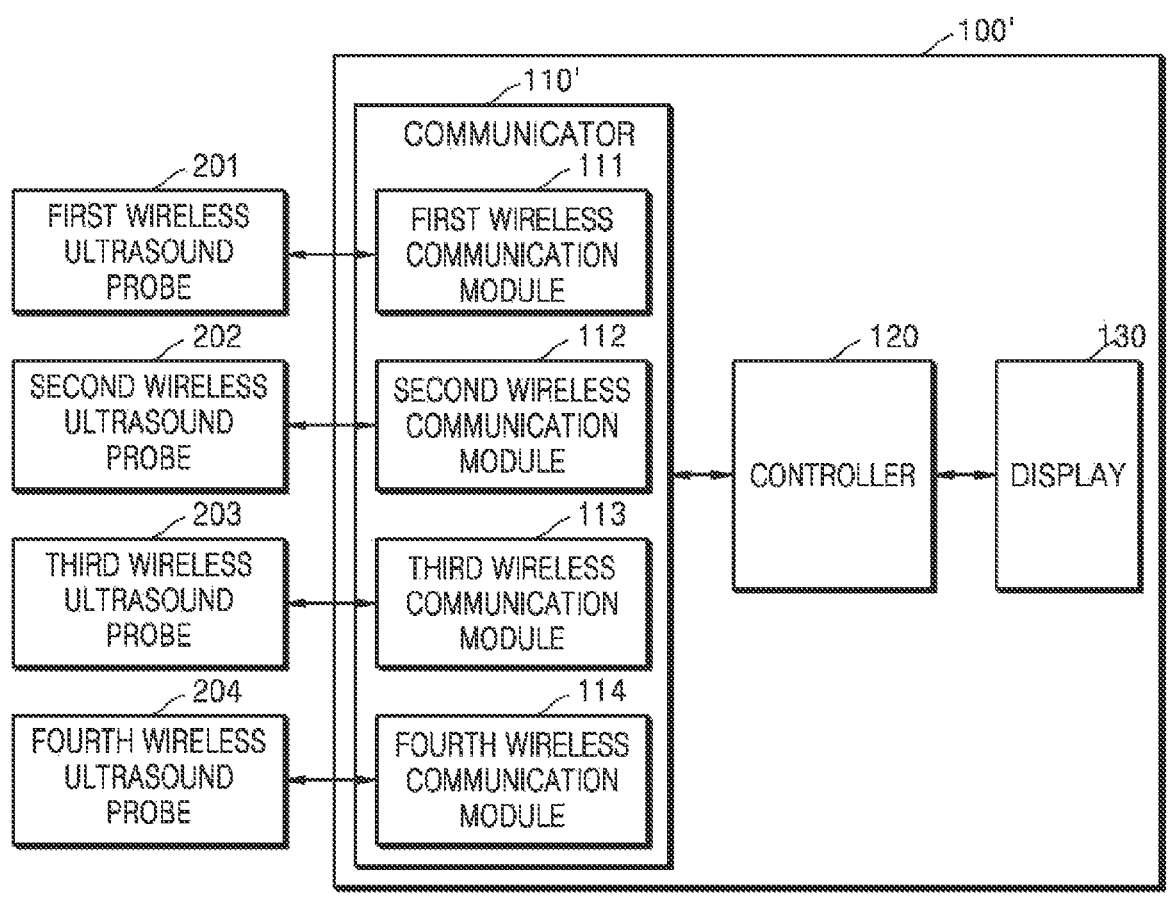
FIG. 3 is a block diagram of a configuration of an ultrasound system according to another embodiment.

FIG. 3 is a block diagram of a configuration of an ultrasound system according to another embodiment.

Referring to FIG. 3, the ultrasound system according to the present embodiment may include an ultrasound diagnosis apparatus 100' and a plurality of wireless ultrasound probes 201 through 204. The ultrasound diagnosis apparatus 100' shown in FIG. 3 includes the same components as the controller 120 and the display 130 of the ultrasound diagnosis apparatus 100 described with reference to FIG. 2, except for a communicator 110', and thus descriptions that are already provided above with respect to FIG. 2 will be omitted here.

The communicator 110' may include first through fourth wireless communication modules 111 through 114. The first through fourth wireless communication modules 111 through 114 may be paired one-to-one with the wireless ultrasound probes 201 through 204 by using at least one of wireless communication methods including WLAN, Wi-Fi, Bluetooth, Zigbee, WFD, IrDA, BLE, NFC, WiBro, WiMAX, SWAP, WiGig, and RF communication. For example, the first through fourth wireless communication modules 111 through 114 may respectively be paired with the first through fourth ultrasound probes 201 through 204.

The first through fourth wireless communication modules 111 through 114 may transmit or receive ultrasound image data to or from the first through fourth wireless ultrasound probes 201 through 204.

Figure 4:
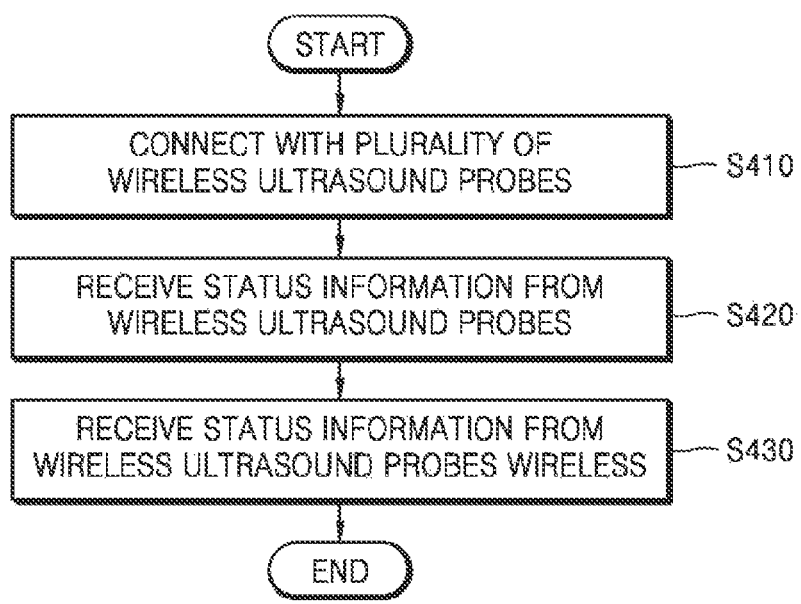
FIG. 4 is a flowchart of a method of operating an ultrasound diagnosis apparatus, according to an embodiment.

FIG. 4 is a flowchart of a method of operating an ultrasound diagnosis apparatus, according to an embodiment.

The ultrasound diagnosis apparatus is connected with a plurality of wireless ultrasound probes by using a wireless communication method (operation S410). The ultrasound diagnosis apparatus may be connected wirelessly with the wireless ultrasound probes by using at least one of wireless communication methods including WLAN, Wi-Fi, Bluetooth, Zigbee, WFD, IrDA, BLE, NFC, WiBro, WiMAX, SWAP, WiGig, and RF communication. In operation S410, when the ultrasound diagnosis apparatus is "connected" with the wireless ultrasound probes, it may mean that the ultrasound diagnosis apparatus is paired to use at least one of the wireless ultrasound probes. According to an embodiment, the wireless ultrasound probes connected to the ultrasound diagnosis apparatus may each be different types of probes having different functions. However, embodiments are not limited thereto.

The ultrasound diagnosis apparatus receives status information from the wireless ultrasound probes (S420). According to an embodiment, the ultrasound diagnosis apparatus may receive, by using a wireless communication method, status information including at least one of ID information, a wireless communication frequency, a connection type, an executable application, a wireless communication method, a communication status, battery charging information, a remaining battery capacity, and a time left for use with respect to each of the paired wireless ultrasound probes.

The ultrasound diagnosis apparatus may display a UI indicating the received status information regarding the wireless ultrasound probes (S430). According to an embodiment, the ultrasound diagnosis apparatus may display a GUI including characters respectively indicating ID information of the wireless ultrasound probes and thumbnail images respectively representing shapes of the wireless ultrasound probes. Furthermore, the ultrasound diagnosis apparatus may display a GUI graphically representing at least one of a wireless communication frequency, a connection type, an executable application, a wireless communication method, a communication status, battery charging information, a remaining battery capacity, and a time left for use with respect to each of the paired wireless ultrasound probes.

Figure 5:
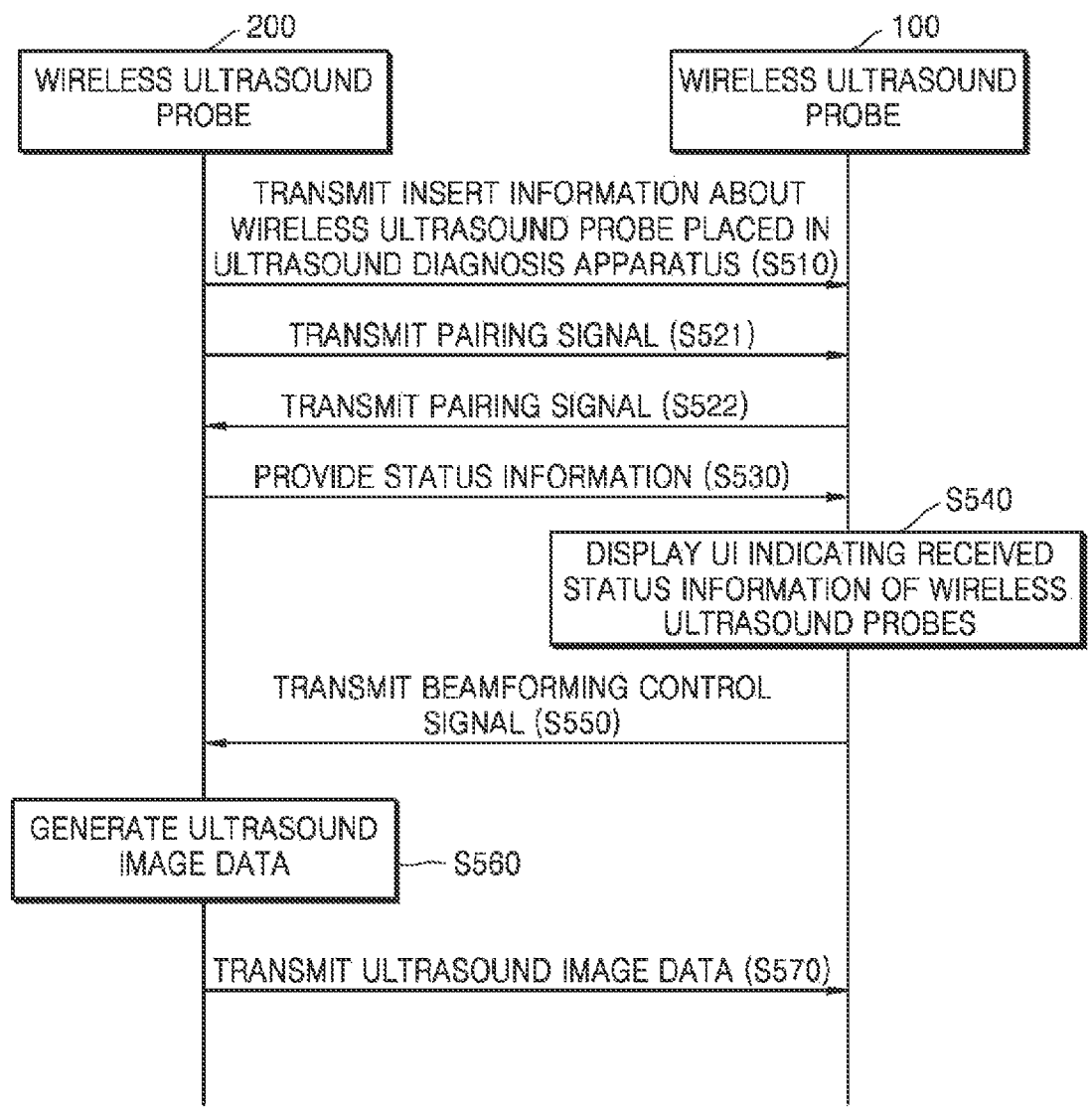
FIG. 5 is a flowchart of a method, performed by an ultrasound diagnosis apparatus, of transmitting or receiving a pairing signal and ultrasound image data to or from a wireless ultrasound probe, according to an embodiment.

FIG. 5 is a flowchart of a method, performed by an ultrasound diagnosis apparatus 100, of transmitting or receiving a pairing signal and ultrasound image data to or from a wireless ultrasound probe 200, according to an embodiment.

The wireless ultrasound probe 200 transmits, to the ultrasound diagnosis apparatus 100, insert information indicating its insertion into the ultrasound diagnosis apparatus 100 (operation S510). In an embodiment, the ultrasound diagnosis apparatus 100 may include a holder into which the wireless ultrasound probe 200 is inserted. When the wireless ultrasound probe 200 is placed in the holder, the ultrasound diagnosis apparatus 100 may receive insert information and recognize the wireless ultrasound probe 200 placed therein based on the received insert information.

According to another embodiment, when the wireless ultrasound probe 200 is located a short distance corresponding to a preset distance from the ultrasound diagnosis apparatus 100, the ultrasound diagnosis apparatus 100 may identify the wireless ultrasound probe 200. For example, when the wireless ultrasound probe 200 includes an NFC communication module, the ultrasound diagnosis apparatus 100 may identify the wireless ultrasound probe 200 by using NFC when the ultrasound diagnosis apparatus 100 is within a preset distance from the wireless ultrasound probe 200.

According to another embodiment, the ultrasound diagnosis apparatus 100 may identify the wireless ultrasound probe 200 based on a user input signal input via a user input device (such as a button) mounted on the wireless ultrasound probe 200, e. g., by using a probe information recognition method based on an RFID, etc.

The wireless ultrasound probe 200 transmits a pairing signal to the ultrasound diagnosis apparatus 100 (operation S521), and the ultrasound diagnosis apparatus 100 transmits a pairing signal to the wireless ultrasound probe 200 (operation S522).

The pairing signals in operations S521 and S522 may be exchanged between the wireless ultrasound probe 200 and the ultrasound diagnosis apparatus 100 by using at least one of wireless communication methods including WLAN, Wi-Fi, Bluetooth, Zigbee, WFD, IrDA, BLE, NFC, WiBro, WiMAX, SWAP, WiGig, and RF communication.

The wireless ultrasound probe 200 provides status information to the ultrasound diagnosis apparatus 100 (operation S530). According to an embodiment, the status information may include at least one of ID information, a wireless communication frequency, a connection type, an executable application, a wireless communication method, a communication status, battery charging information, a remaining battery capacity, and a time left for use with respect the wireless ultrasound probe 200. The wireless ultrasound probe 200 may transmit the status information to the ultrasound diagnosis apparatus 100 by using a wireless communication method.

The ultrasound diagnosis apparatus 100 displays a UI indicating the received status information regarding the wireless ultrasound probe 200 (operation S540). In an embodiment, the ultrasound diagnosis apparatus 100 may display a GUI indicating the status information on a display.

The ultrasound diagnosis apparatus 100 transmits a beamforming control signal to the wireless ultrasound probe 200 (operation S550). According to an embodiment, the wireless ultrasound probe 200 may be an ultrasound probe having a beamformer therein, and the ultrasound diagnosis apparatus 100 may transmit to the wireless ultrasound probe 200 a signal for controlling the beamformer provided in the wireless ultrasound probe 200 to irradiate ultrasound signals towards an object by using a wireless communication method.

The wireless ultrasound probe 200 transmits ultrasound signals to the object based on the received beamforming control signal and generates ultrasound image data based on ultrasound echo signals reflected from the object (operation S560).

The wireless ultrasound probe 200 transmits the generated ultrasound image data to the ultrasound diagnosis apparatus 100 (operation S570). According to an embodiment, the wireless ultrasound probe 200 may transmit the ultrasound image data generated by performing analog-to-digital conversion on ultrasound raw data regarding the object to the ultrasound diagnosis apparatus 100 by using a 60-GHz local area wireless communication method. In another embodiment, the wireless ultrasound probe 200 may generate a final ultrasound image based on the ultrasound image data regarding the object and transmit the generated final ultrasound image to the ultrasound diagnosis apparatus 100 by using a wireless communication method such as Wi-fi, Bluetooth, etc.

Figure 6:
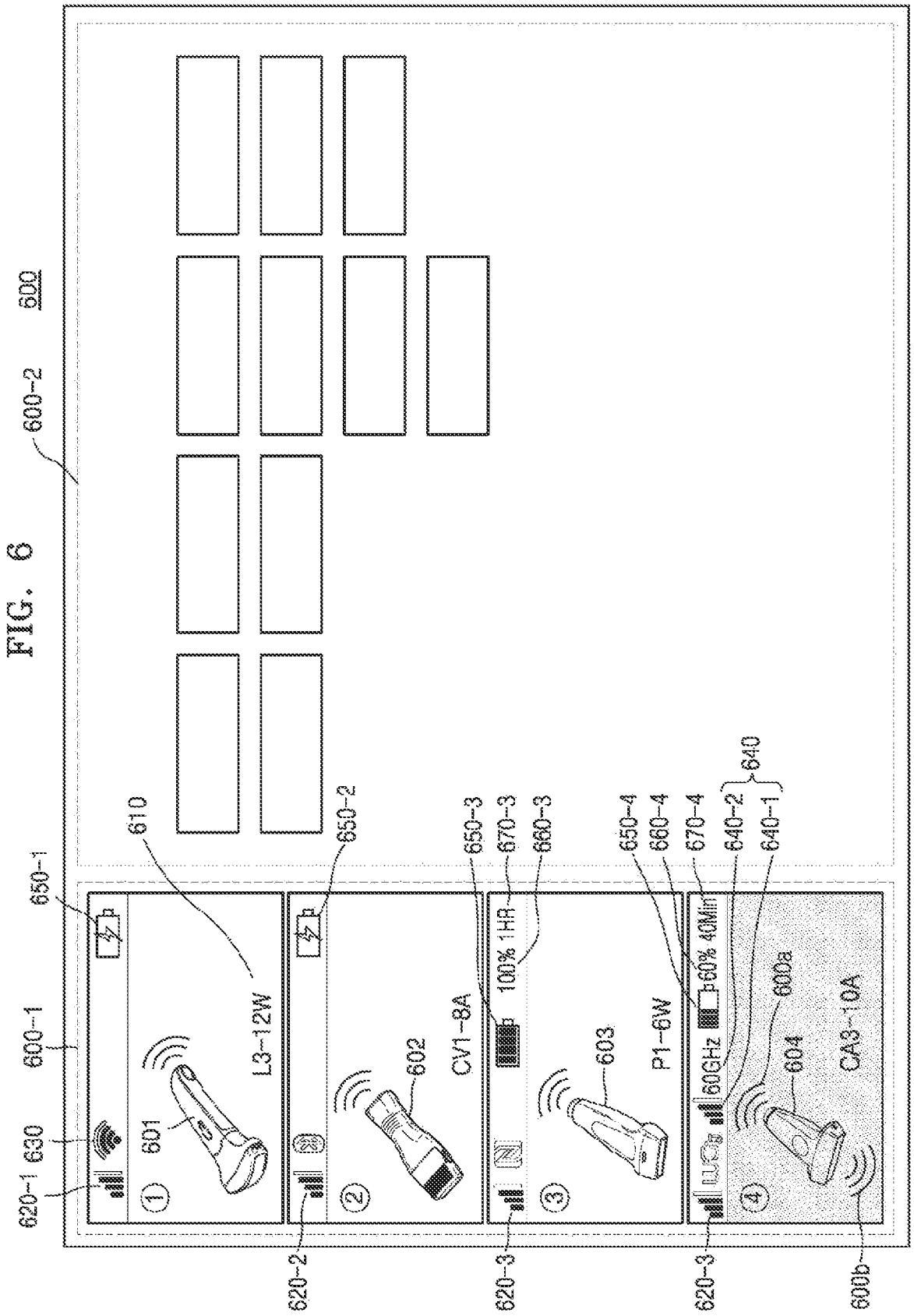
FIG. 6 illustrates an example in which an ultrasound diagnosis apparatus displays status information regarding a plurality of wireless ultrasound probes connected thereto, according to an embodiment.

FIG. 6 illustrates an example in which an ultrasound diagnosis apparatus displays status information regarding a plurality of wireless ultrasound probes, i.e., first through fourth wireless ultrasound probes 601 through 604 connected thereto, according to an embodiment.

Referring to FIG. 6, a display 600 may display in a first region 600-1 a UI including thumbnail images respectively representing shapes of the first through fourth wireless ultrasound probes 601 through 604 connected to the ultrasound diagnosis apparatus and characters respectively indicating ID information of the first through fourth wireless ultrasound probes 601 through 604. As a component of the ultrasound diagnosis apparatus, the display 600 may be attached to a control panel to display a UI, but embodiments are not limited thereto. The display 600 may display an ultrasound image of an object via one of the first through fourth wireless ultrasound probes 601 through 604. The display 600 may display in a second region 600-2 UIs used for operating the ultrasound diagnosis apparatus, e.g., for obtaining an ultrasound image of the object or manipulating the obtained ultrasound image by using the ultrasound diagnosis apparatus.

A UI indicating status information regarding the first through fourth wireless ultrasound probes 601 through 604 wirelessly paired to the ultrasound diagnosis apparatus may be displayed in the first region 600-1. In an embodiment, the UI may be a GUI graphically representing status information. For example, the status information may include at least one of a wireless connection status, a wireless communication method, a wireless communication frequency, and a connection type with respect to each of the first through fourth wireless ultrasound probes 601 through 604.

For example, a first UI 610 indicating ID information of the first wireless ultrasound probe 601, a second UI 620-1 indicating a status of wireless connection between the first wireless ultrasound probe 601 and the ultrasound diagnosis apparatus, and a third UI 630 indicating a wireless communication method used to pair the first wireless ultrasound probe 601 with the ultrasound diagnosis apparatus may be displayed in the first region 600-1 of the display 600. The first UI 610 indicating the ID information of the first wireless ultrasound probe 601 may be displayed as characters, but the second UI 620-1 may be a GUI indicating a wireless connection status as the number of bar-shaped antennas. The third UI 630 may be a GUI composed of symbols indicating Wi-fi, Bluetooth, NFC, WiGig, etc. The number of bars in the second UI 620-1 and the number of antennas in the third UI 630 may be symbols that graphically represent a status of wireless communication between the first wireless ultrasound probe 601 and the ultrasound diagnosis apparatus. For example, in the third UI 630 indicating pairing via Wi-fi, the more antennas that are filled in a fan-shaped antenna symbol may mean the smoother Wi-fi pairing between the first wireless ultrasound probe 601 and the ultrasound diagnosis apparatus.

In the embodiment shown in FIG. 6, the second through fourth wireless ultrasound probes 602 through 604 may be wirelessly paired with the ultrasound diagnosis apparatus by using Bluetooth, NFC, and WiGig, respectively. Statuses of wireless communications between each of the second through fourth wireless ultrasound probes 602 through 604 and the ultrasound diagnosis apparatus may respectively be displayed via first UIs 620-2 through 620-4.

A fourth UI 640 indicating a method of data communication between the ultrasound diagnosis apparatus and the fourth wireless ultrasound probe 604 activated among the first through fourth wireless ultrasound probes 610 through 602 may be displayed in the first region 600-1. A thumbnail image of the fourth wireless ultrasound probe 604 that is the activated wireless ultrasound probe and its neighborhood may be shown in a specific color or shade to distinguish the fourth wireless ultrasound probe 604 from the first through third wireless ultrasound probes 601 through 603 that are not activated. According to an embodiment, a UI 600*a* representing a state of wireless pairing with the ultrasound diagnosis apparatus and a UI 600*b* representing a state in which an ultrasound signal is being transmitted to the object, i.e., an activated state, may be indicated on the thumbnail image of the fourth wireless ultrasound probe 604.

According to an embodiment, the fourth wireless ultrasound probe 604 may transmit ultrasound signals to the object, receive ultrasound echo signals reflected from the object, and perform analog-to-digital conversion on the ultrasound echo signals to thereby generate ultrasound raw data. The fourth wireless ultrasound probe 604 may transmit the ultrasound raw data to the ultrasound diagnosis apparatus by using a 60-GHz mmWave data communication method. In this case, a fourth UI 640 may include a UI 640-1 indicating a status of data communication between the fourth ultrasound probe 604 and the ultrasound diagnosis apparatus and a UI 640-2 indicating a method of transmission of ultrasound raw data as "60 GHz". The fourth UI 640 may be displayed on one side of the thumbnail image of the fourth wireless ultrasound probe 604 that is the activated wireless ultrasound probe.

Furthermore, the display 600 may display in the first region 600-1 a UI indicating a state of a battery embedded in each of the first through fourth wireless ultrasound probes 601 through 604 connected to the ultrasound diagnosis apparatus, whether the battery is being charged, a time left for use, etc. For example, fifth UIs 650-1 and 650-2 respectively indicating that batteries respectively embedded in the first and second wireless ultrasound probes 601 and 602 are being charged may be displayed in the first region 600-1. In the embodiment shown in FIG. 6, the fifth UIs 650-1 and 650-2 may allow the user to easily identify that the first and second wireless ultrasound probes 601 and 602 are being charged.

In an embodiment, a battery embedded in the third wireless ultrasound probe 603 may be fully charged to 100% while a battery in the fourth wireless ultrasound probe 604 may have 60% charge left. In this case, the display 600 may display fifth UIs 650-3 and 650-4 indicating the remaining battery capacities of the third and fourth wireless ultrasound probes 603 and 604 as geometric shapes or symbols and sixth UIs 660-3 and 660-4 indicating them as percentage (%) figures or characters.

According to an embodiment, the display 600 may display seventh UIs 670-3 and 670-4 respectively indicating remaining usable times of the third and fourth wireless ultrasound probes 603 and 604.

While FIG. 6 shows that the display 600 simultaneously displays second UIs 620-1 through 620-4 indicating a wireless connection status, the third UI 630 indicating a wireless communication method, the fourth UI 640 indicating a wireless communication frequency, the fifth UIs 650-1 and 650-2 indicating whether batteries are being charged, the fifth UIs 650-3 and 650-4 and sixth UIs 660-3 and 660-4 indicating remaining battery capacities, and the seventh UIs 670-3 and 670-4 indicating remaining usable times, embodiments are not limited thereto. In an embodiment, status information may include at least one of ID information, a wireless communication frequency, a connection type, a supported application, a wireless communication method, a communication status, battery charging information, a remaining battery capacity, and a time left for use with respect to each of the first through fourth wireless ultrasound probes 601 through 604 paired to the ultrasound diagnosis apparatus by using a wireless communication method. Furthermore, UIs indicating the above status information may be displayed simultaneously or separately.

Figure 7A:
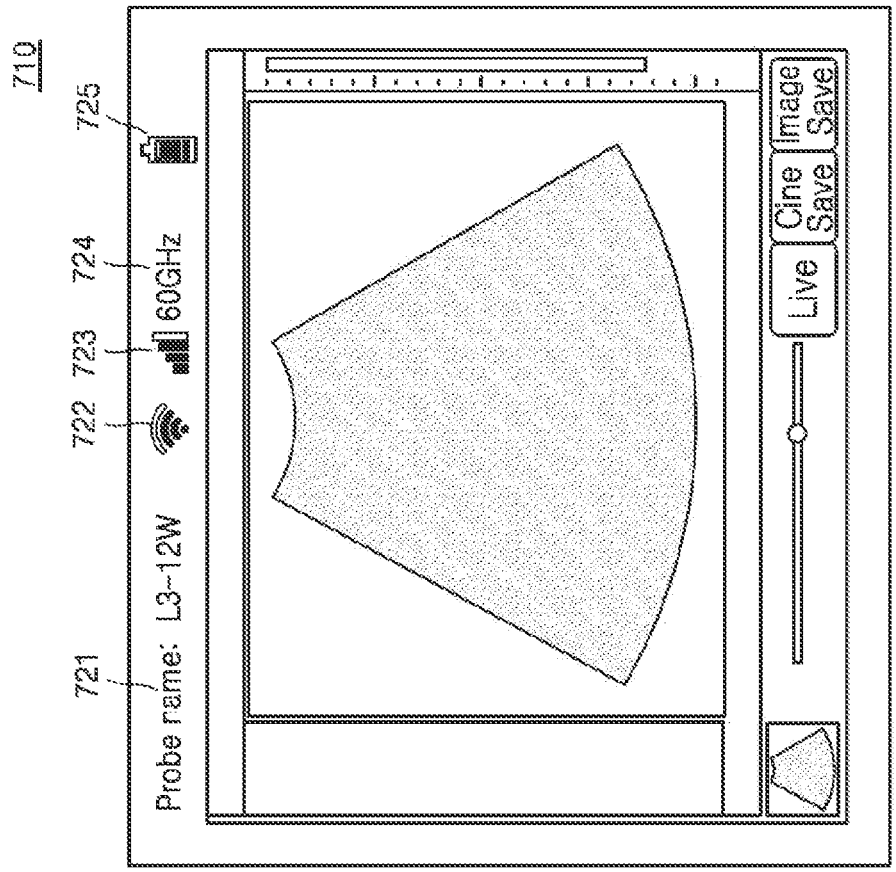
FIGS. 7A and 7B are diagrams illustrating examples in which an ultrasound diagnosis apparatus displays information about a status of its communication with a plurality of wireless ultrasound probes connected thereto, according to embodiments.
Figure 7B:
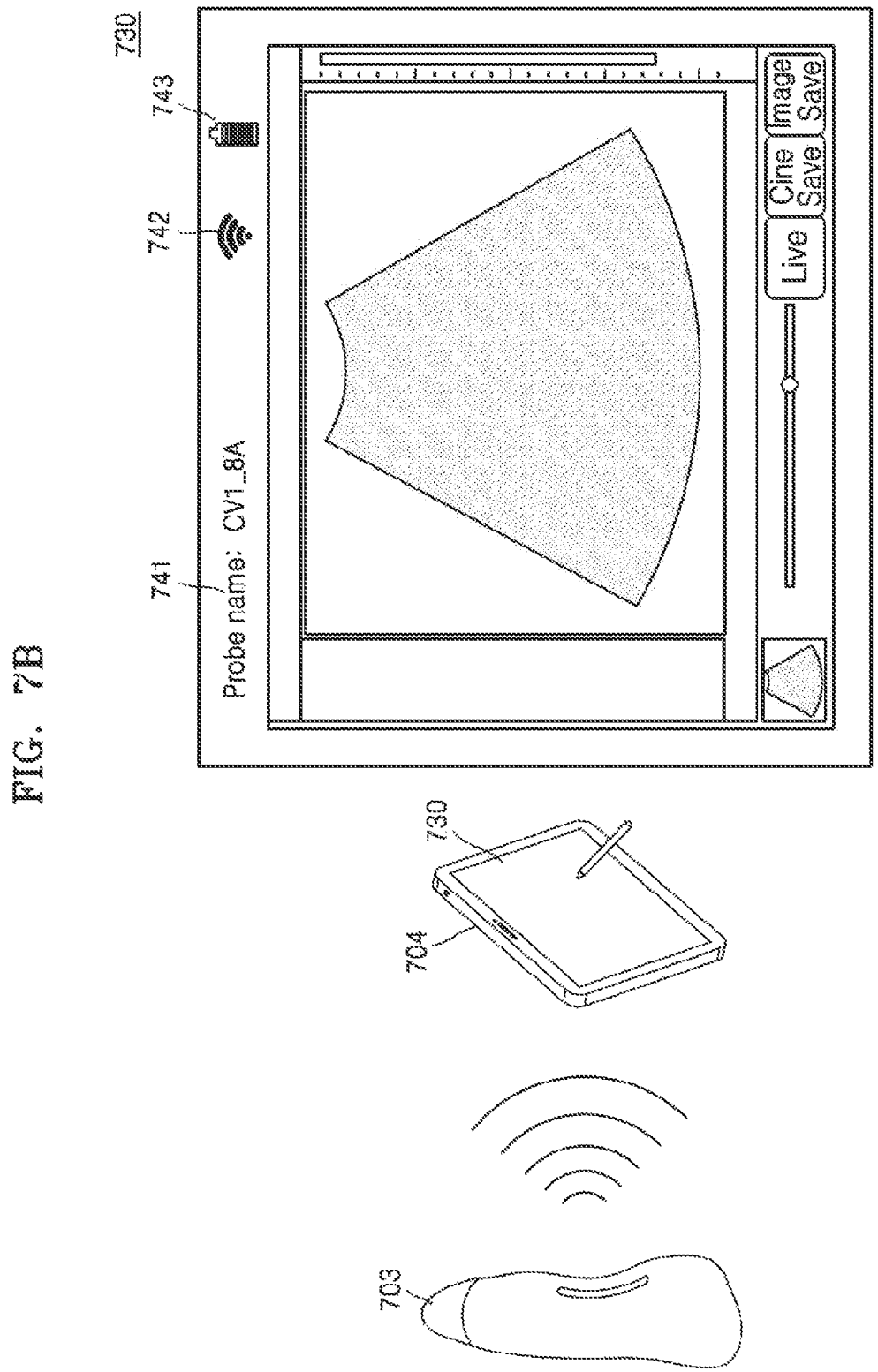

FIGS. 7A and 7B are diagrams illustrating examples in which an ultrasound diagnosis apparatus displays information about a status of its communication with a plurality of wireless ultrasound probes connected thereto, according to embodiments.

Referring to FIG. 7A, a wireless ultrasound probe 701 may be connected wirelessly to an ultrasound diagnosis apparatus 700. In an embodiment, the ultrasound diagnosis apparatus 702 may be a cart type apparatus, but is not limited thereto.

According to an embodiment, the wireless ultrasound probe 701 may be wirelessly paired to the ultrasound diagnosis apparatus 702 by using a communication method such as Wi-fi, WLAN, or Bluetooth. Furthermore, the wireless ultrasound probe 701 may transmit ultrasound raw data generated using ultrasound echo signals acquired from the object to the ultrasound diagnosis apparatus 702. In this case, the wireless ultrasound probe 701 may transmit the ultrasound raw data wirelessly to the ultrasound diagnosis apparatus 702 by using a 60-GHz mmWave data communication method. The ultrasound diagnosis apparatus 702 may perform image processing on the received ultrasound raw data to generate an ultrasound image.

A display 710 of the ultrasound diagnosis apparatus 702 may display first through fifth UIs 721 through 725 indicating status information of the wireless ultrasound probe 701. For example, the display 710 may display the first UI 721 indicating ID information of the wireless ultrasound probe 701, the second UI 722 indicating a method of pairing with the wireless ultrasound probe 701, the third UI 723 indicating a status of data communication between the wireless ultrasound probe 701 and the ultrasound diagnosis apparatus 702, the fourth UI 724 indicating a method of performing data communication with the ultrasound diagnosis apparatus 702, and the fifth UI 725 indicating a status of a battery in the wireless ultrasound probe 701.

Although the second and fourth UIs 722 and 724 both indicate methods of wireless communication between the ultrasound diagnosis apparatus 702 and the wireless ultrasound probe 701, they actually indicate different types of communication methods. In detail, the second UI 722 indicates a wireless communication method such as Wi-fi, Bluetooth, etc., via which the wireless ultrasound probe 701 is wirelessly paired to the ultrasound diagnosis apparatus 702, whereas the fourth UI 724 indicates a data communication method for transmitting ultrasound raw data generated by the wireless ultrasound probe 701 to the ultrasound diagnosis apparatus 702.

The second UI 722 and a third UI 723 may both indicate a status of wireless communication between the wireless ultrasound probe 701 and the ultrasound diagnosis apparatus 702. For example, the second UI 722 may indicate that the ultrasound diagnosis apparatus 702 is wirelessly paired with the wireless ultrasound probe 701 via Wi-fi while simultaneously displaying a status of the wireless pairing. In other words, when the number of fan-shaped antennas in the second UI 722 increases, it may mean that wireless pairing is performed more smoothly. Similarly, the third UI 723 may indicate status information about data communication between the wireless ultrasound probe 701 and the ultrasound diagnosis apparatus 702 based on the number of bar-shaped antennas. For example, as the number of bar-shaped antennas in the third UI 723 increases, ultrasound raw data generated by the wireless ultrasound probe 701 may be transmitted to the ultrasound diagnosis apparatus 702 more smoothly.

Referring to FIG. 7B, a wireless ultrasound probe 703 may be wirelessly connected to an ultrasound imaging apparatus 704. In an embodiment, the ultrasound imaging apparatus 704 may be a tablet pc, but is not limited thereto.

The wireless ultrasound probe 703 may be paired with the ultrasound imaging apparatus 704 by using a communication method such as Wi-fi or Bluetooth. The wireless ultrasound probe 703 may include both a beamformer and an image processor, and perform analog-to-digital conversion of ultrasound echo signals and then post-processing of the resulting signals to thereby generate ultrasound image data regarding an object. In this case, the wireless ultrasound probe 703 may transmit the ultrasound image data to the ultrasound imaging apparatus 704 by using a local area wireless communication method such as Wi-fi, WLAN, or Bluetooth. The wireless ultrasound probe 703 may transmit data having a resolution suitable for a table PC to the ultrasound diagnosis apparatus 704 after performing additional image processing on ultrasound raw data.

A display 730 of the ultrasound imaging apparatus 704 may display UIs 741 through 743 indicating status information of the wireless ultrasound probe 703. For example, the display 730 may display the first UI 741 indicating ID information of the wireless ultrasound probe 703, the second UI 742 indicating a method of pairing and data communication with the wireless ultrasound probe 703, and the third UI 743 indicating a status of a battery in the wireless ultrasound probe 703. Unlike the second UI 722 described with reference to FIG. 7A, the second UI 742 may indicate both a method of wireless pairing between the wireless ultrasound probe 703 and the ultrasound imaging apparatus 704 and a method of communicating ultrasound image data therebetween.

In the embodiments shown in FIGS. 7A and 7B, the wireless ultrasound probe 701 and 703 may generate only ultrasound raw data regarding the object or acquire ultrasound image data by performing post-processing of the ultrasound raw data and transmit the ultrasound raw data and the ultrasound image data respectively to the ultrasound diagnosis apparatus 702 and the ultrasound imaging apparatus 704. The wireless ultrasound probe 701 according to the embodiment shown in FIG. 7A transmits to the ultrasound diagnosis apparatus 702 ultrasound raw data with higher image quality and higher frame rate than in the embodiment shown in FIG. 7B. Thus, the wireless ultrasound probe 701 may use a 60-GHz mmWave data communication method for the transmission. In the embodiment shown in FIG. 7B, the wireless ultrasound probe 703 generates ultrasound image data with low image quality and low frame rate by performing post-processing of ultrasound raw data and transmits the ultrasound image data to the ultrasound imaging apparatus 704 such as a tablet PC. In this case, the wireless ultrasound probe 703 may use a communication method such as Wi-fi or Bluetooth for the transmission.

According to the embodiments described with reference to FIGS. 7A and 7B, when the wireless ultrasound probes 701 and 703 transmits ultrasound raw data or ultrasound image data by using different types of communication methods, UIs (722 and 723 of FIG. 7A and 742 of FIG. 7B) indicating data communication methods are respectively displayed on the displays 710 and 730. This allows the user to easily identify a data communication method, thereby increasing user convenience.

Figure 8:
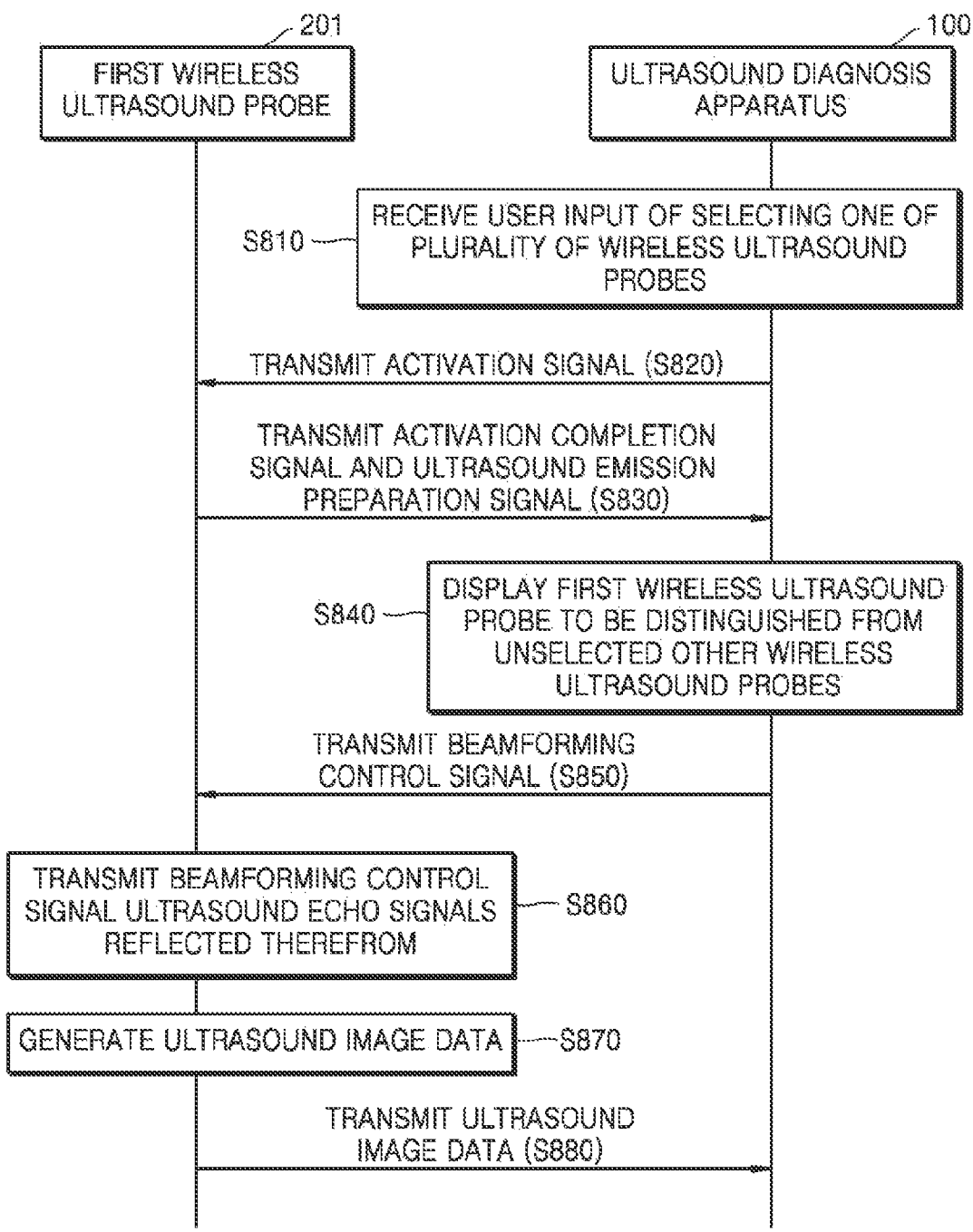
FIG. 8 is a flowchart of a method, performed by an ultrasound diagnosis apparatus, of acquiring ultrasound image data by using a wireless ultrasound probe selected based on a user input, according to an embodiment.

FIG. 8 is a flowchart of a method, performed by an ultrasound diagnosis apparatus 100, of acquiring ultrasound image data by using a first wireless ultrasound probe 201 selected based on a user input, according to an embodiment.

The ultrasound diagnosis apparatus 100 receives a user input for using at least one of a plurality of wireless ultrasound probes (operation S810). According to an embodiment, the ultrasound diagnosis apparatus 100 may include a user input interface for receiving a user input. The user input interface may include hardware components such as a key pad, a mouse, a trackball, a touch pad, a touch screen, and a jog switch, but are not limited thereto. In operation S810, the ultrasound diagnosis apparatus 100 may receive a user input of selecting the first wireless ultrasound probe 201 among the plurality of wireless ultrasound probes via the user input interface.

The ultrasound diagnosis apparatus 100 transmits an activation signal to the first wireless ultrasound probe 201 (operation S820). In this case, an "activation signal" is a signal for operating the first wireless ultrasound probe 201 selected based on the user input to transmit ultrasound signals to an object and receive ultrasound echo signals reflected from the object. The activation signal is different from a pairing signal (operation 521 of FIG. 5) for simply connecting the ultrasound diagnosis apparatus 100 with the first wireless ultrasound probe 201 in a wireless manner.

According to an embodiment, the ultrasound diagnosis apparatus 100 may transmit the activation signal to the first wireless ultrasound probe 201 by using at least one of wireless data communication techniques including a WLAN, Wi-Fi, Bluetooth, Zigbee, WFD, IrDA, BLE, NFC, WiBro, WiMAX, SWAP, WiGig, and RF communication.

The first wireless ultrasound probe 201 transmits an activation completion signal and an ultrasound emission preparation signal to the ultrasound diagnosis apparatus 100 (operation S830).

The ultrasound diagnosis apparatus 100 displays the first wireless ultrasound probe 201 to be distinguished from the unselected other wireless ultrasound probes (operation S840). In an embodiment, the ultrasound diagnosis apparatus 100 may include a display configure to display a UI indicating ID information and thumbnail images of the wireless ultrasound probes including the first wireless ultrasound probe 201. The display may display the first wireless ultrasound probe 201 that has transmitted the activation signal and the ultrasound emission preparation signal to be distinguished from the other wireless ultrasound probes, e. g., by using a different color, by adding a shade therein, or by displaying ID information in bold characters.

The ultrasound diagnosis apparatus 100 transmits a beamforming control signal to the first wireless ultrasound probe 201 (operation S850). According to an embodiment, the first wireless ultrasound probe 201 may be an ultrasound probe having a beamformer therein, and the ultrasound diagnosis apparatus 100 may transmit to the wireless ultrasound probe 201 a signal for controlling the beamformer provided in the first wireless ultrasound probe 201 to irradiate ultrasound signals towards the object by using a wireless communication method.

The first wireless ultrasound probe 201 transmits ultrasound signals to the object based on the received beamforming control signal and receives ultrasound echo signals reflected from the object (operation S860).

The first wireless ultrasound probe 201 generates ultrasound image data by performing image processing on the received ultrasound echo signals (operation S870).

The first wireless ultrasound probe 201 transmits the generated ultrasound image data to the ultrasound diagnosis apparatus 100 (operation S880). According to an embodiment, the first wireless ultrasound probe 201 may transmit the ultrasound image data generated by performing analog-to-digital conversion on ultrasound raw data regarding the object to the ultrasound diagnosis apparatus 100 by using a 60-GHz local area wireless communication method. In another embodiment, the first wireless ultrasound probe 201 may generate a final ultrasound image based on the ultrasound image data regarding the object and transmit the generated final ultrasound image to the ultrasound diagnosis apparatus 100 by using a wireless communication method such as Wi-fi, Bluetooth, etc.

Figure 9:
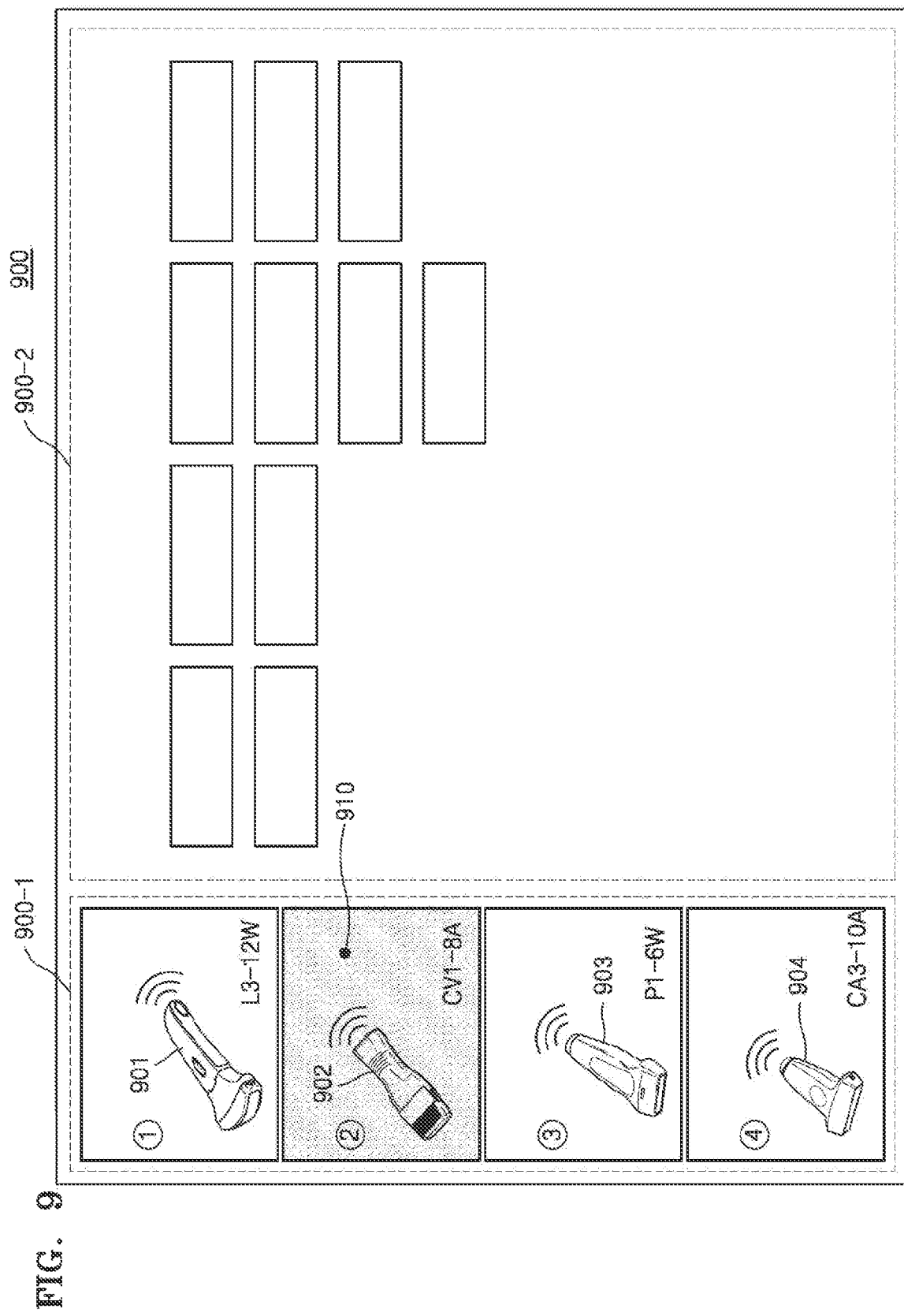
FIG. 9 illustrates a user interface (UI) indicating a wireless ultrasound probe activated among a plurality of wireless ultrasound probes, based on a user input, according to an embodiment.

FIG. 9 illustrates a UI displayed on a display 900 of an ultrasound diagnosis apparatus, the UI indicating a second wireless ultrasound probe 902 activated among a plurality of wireless ultrasound probes, i.e., first through fourth wireless ultrasound probes 901 through 904 based on a user input, according to an embodiment.

Referring to FIG. 9, the display 900 may display only the second wireless ultrasound probe 902, which is activated among the first through fourth wireless ultrasound probes 901 through 904 based on a user input, to be distinguished from the other wireless ultrasound probes, i.e., the first, third, and fourth wireless ultrasound probes 901, 903, and 904. According to an embodiment, the display 900 may display only a region including ID information and a thumbnail image of the second wireless ultrasound probe 902 in shade or in a different color from those for regions showing the other wireless ultrasound probes 901, 903, and 904. Furthermore, the display 900 may display an activation UI 910 indicating an activated wireless ultrasound probe in the region where the ID information and the thumbnail image of the second wireless ultrasound probe 902 are displayed. Although not shown in FIG. 9, the display 900 may display characters representing the ID information of the activated second wireless ultrasound probe 902 in bold type unlike for those representing ID information of the other wireless ultrasound probes 901, 903, and 904.

According to the embodiment described with reference to FIG. 9, the user may intuitively identify only the currently activated second wireless ultrasound probe 902 from among the first through fourth wireless ultrasound probes 901 through 904 that are wirelessly paired to the ultrasound diagnosis apparatus.

Figure 10:
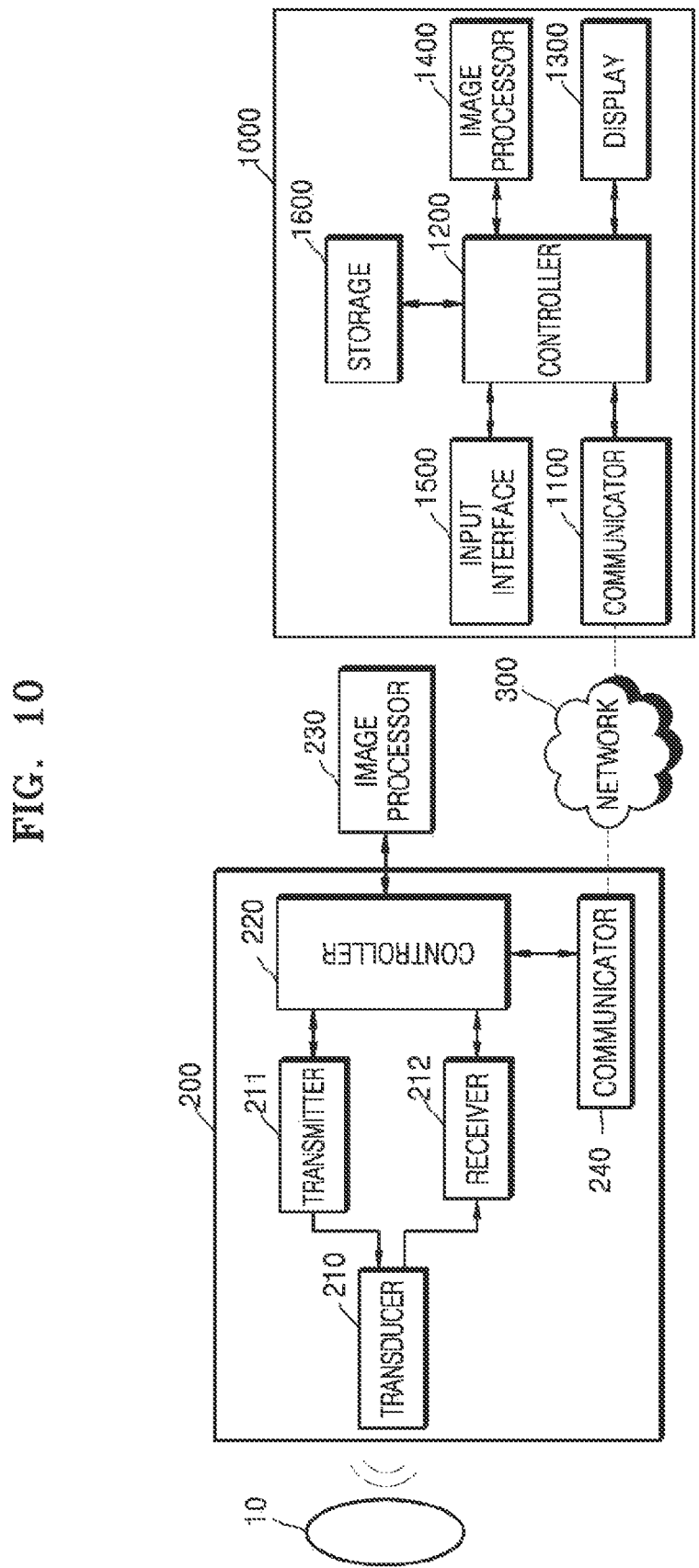
FIG. 10 is a block diagram of a configuration of an ultrasound diagnosis apparatus including a wireless ultrasound probe, according to an embodiment.

FIG. 10 is a block diagram of a configuration of an ultrasound diagnosis apparatus 1000 including a wireless ultrasound probe 200, according to an embodiment.

Referring to FIG. 10, the ultrasound diagnosis apparatus 1000 may be connected with a wireless ultrasound probe 200 via a network 300.

The wireless ultrasound probe 200 may include a transmitter 211, a transducer 210, a receiver 212, a controller 220, an image processor 230, and a communicator 240. Although FIG. 10 shows that the wireless ultrasound probe 200 includes both the transmitter 211 and the receiver 212, according to an implemented configuration, the wireless ultrasound probe 200 may include some of the components of the transmitter 211 and the receiver 212 while the ultrasound diagnosis apparatus 1000 may also include some of them.

The transducer 210 may include a plurality of transducer elements. The plurality of transducer elements 211 transmit ultrasound signals to an object 10 in response to transmitting signals received from the transmitter 211. The transducer elements may receive ultrasound signals reflected from the object 10 to generate reception signals.

The controller 220 controls the transmitter 211 to generate transmitting signals to be respectively applied to the transducer elements based on a position and a focal point of the transducer elements.

The controller 220 controls the receiver 212 to generate ultrasound data by performing analog-to-digital conversion on the reception signals received from the transducer 210 and summing the analog-to-digital converted reception signals based on a position and a focal point of the transducer elements.

The image processor 230 may generate an ultrasound image based on the generated ultrasound data.

The communicator 240 may wirelessly transmit the generated ultrasound data or ultrasound image to the ultrasound diagnosis apparatus 1000 via a wireless network. Alternatively, the communicator 240 may receive a control signal and data from the ultrasound diagnosis apparatus 1000.

The ultrasound diagnosis apparatus 1000 may receive ultrasound data or an ultrasound image from the wireless ultrasound probe 200. The ultrasound diagnosis apparatus 1000 may include a communicator 1100, a controller 1200, a display 1300, an image processor 1400, an input interface 1500, and a storage 1600.

The controller 1200 may control all operations of the ultrasound diagnosis apparatus 1000 and flow of signals between the internal elements of the ultrasound diagnosis apparatus 1000. The controller 1200 may include a memory for storing a program or data to perform functions of the ultrasound diagnosis apparatus 1000 and a processor for processing the program or data. Furthermore, the controller 1200 may control the operation of the ultrasound diagnosis apparatus 1000 by receiving a control signal from the input interface 1500 or an external apparatus.

The ultrasound diagnosis apparatus 1000 may include the communicator 1100 and may be connected to external apparatuses, for example, servers, medical apparatuses, and portable devices such as smart phones, tablet PCs, wearable devices, etc., via the communicator 1100.

The communicator 1100 may include at least one element capable of communicating with the external apparatuses. For example, the communicator 1100 may include at least one of a local area communication module, a wired communication module, and a wireless communication module.

The communicator 1100 may receive a control signal and data from an external apparatus and transmit the received control signal to the controller 1200 such that the controller 1200 may control the ultrasound diagnosis apparatus 1000 in response to the received control signal.

Alternatively, the controller 1200 may transmit a control signal to the external apparatus via the communicator 1100 to control the external apparatus in response to the control signal from the controller 1200.

For example, the external apparatus may process data from the external apparatus in response to the control signal from the controller 1200 received via the communicator 1100.

A program for controlling the ultrasound diagnosis apparatus 1000 may be installed in the external apparatus. The program may include command languages for performing part of operation of the controller 1200 or the entire operation thereof.

The program may be pre-installed in the external apparatus or may be installed by a user of the external apparatus by downloading the program from a server that provides applications. The server that provides applications may include a recording medium on which the program is stored.

The image processor 1400 may generate an ultrasound image by using ultrasound data received from the wireless ultrasound probe 200.

The display 1300 may display an ultrasound image received from the wireless ultrasound probe 200 and an ultrasound image generated by the ultrasound diagnosis apparatus 1000. The ultrasound diagnosis apparatus 1000 may include two or more displays 1300 according to its implemented configuration. Furthermore, the display 1300 may be combined with a touch panel to form a touch screen.

The storage 1600 may store various data or programs for driving and controlling the ultrasound diagnosis apparatus 1000, input and/or output ultrasound data, ultrasound images, etc.

The input interface 1500 receives a user input for controlling the ultrasound diagnosis apparatus 1000. For example, the user input may include an input for manipulating a button, a keypad, a mouse, a trackball, a jog switch, or a knop, an input for touching a touchpad or a touch screen, a voice input, a motion input, and an input of biometric information such as iris recognition or fingerprint recognition, but embodiments are not limited thereto.

Examples of the ultrasound diagnosis apparatus 1000 according to an embodiment will now be described in detail with reference to FIGS. 11A through 11C.

FIGS. 11A, 11B, and 11C are diagrams illustrating ultrasound diagnosis apparatuses according to an exemplary embodiment.

Referring to FIGS. 11A and 11B, the ultrasound diagnosis apparatuses 1000a and 1000b may include a main display 1210 and a sub-display 1220. At least one among the main display 1210 and the sub-display 1220 may include a touch screen. The main display 1210 and the sub-display 1220 may display ultrasound images and/or various information processed by the ultrasound diagnosis apparatuses 1000*a* and 1000*b*. The main display 1210 and the sub-display 1220 may provide graphical user interfaces (GUI), thereby receiving user's inputs of data to control the ultrasound diagnosis apparatuses 1000*a* and 1000*b*. For example, the main display 1210 may display an ultrasound image and the sub-display 1220 may display a control panel to control display of the ultrasound image as a GUI. The sub-display 1220 may receive an input of data to control the display of an image through the control panel displayed as a GUI. The ultrasound diagnosis apparatuses 1000*a* and 1000*b* may control the display of the ultrasound image on the main display 1210 by using the input control data.

Referring to FIG. 11B, the ultrasound diagnosis apparatus 1000*b* may include a control panel 1650. The control panel 1650 may include buttons, trackballs, jog switches, or knobs, and may receive data to control the ultrasound diagnosis apparatus 1000*b* from the user. For example, the control panel 1650 may include a time gain compensation (TGC) button 1710 and a freeze button 1720. The TGC button 1710 is to set a TGC value for each depth of an ultrasound image. Also, when an input of the freeze button 1720 is detected during scanning an ultrasound image, the ultrasound diagnosis apparatus 1000*b* may keep displaying a frame image at that time point.

The buttons, trackballs, jog switches, and knobs included in the control panel 1650 may be provided as a GUI to the main display 1210 or the sub-display 1220.

Referring to FIG. 11C, the ultrasound diagnosis apparatus 1000*c* may include a portable device. An example of the portable ultrasound diagnosis apparatus 1000*c* may include, for example, smart phones including probes and applications, laptop computers, personal digital assistants (PDAs), or tablet PCs, but an exemplary embodiment is not limited thereto.

The ultrasound diagnosis apparatus 1000*c* may include the probe 2000 and a main body 3000. The probe 2000 may be connected to one side of the main body 3000 by wire or wirelessly. The main body 3000 may include a touch screen 1450. The touch screen 1450 may display an ultrasound image, various pieces of information processed by the ultrasound diagnosis apparatus 1000*c*, and a GUI.

The embodiments of the present invention can be written as computer programs and can be implemented in general-use digital computers that execute the programs using a computer-readable recording medium. The above-described embodiments of the present disclosure may be embodied in form of a computer-readable recording medium for storing computer executable command languages and data. The command languages may be stored in form of program codes and, when executed by a processor, may perform a certain operation by generating a certain program module. Also, when executed by a processor, the command languages may perform certain operations of the disclosed embodiments.

Examples of the computer-readable recording medium include magnetic storage media (e.g., ROM, floppy disks, hard disks, etc.), optical recording media (e.g., CD-ROMs or DVDs), etc.

While the present invention has been particularly shown and described with reference to exemplary embodiments thereof, it will be understood by those of ordinary skill in the art that various changes in form and details may be made therein without departing from the spirit and scope of the present invention as defined by the following claims. Accordingly, the above embodiments and all aspects thereof are examples only and are not limiting.

What is claimed is:

1. An electronic device comprising:
    a display;
    a first communicator configured to wirelessly pair with a wireless ultrasound probe;
    a second communicator configured to receive ultrasound image data from the wireless ultrasound probe; and
    a controller configured to:
    in response to receiving a first user input for searching the wireless ultrasound probe, control the first communicator to output a pairing signal,
    in response to the first communicator being paired with the wireless ultrasound probe and receiving identification (ID) information of the paired wireless ultrasound probe, control the display to display the ID information of the paired wireless ultrasound probe, and
    in response to receiving a second user input for activating the paired wireless ultrasound probe, control the first communicator or the second communicator to transmit an activation signal to the paired wireless ultrasound probe and control the second communicator to receive the ultrasound image data from the paired wireless ultrasound probe.

2. The electronic device of claim 1, wherein the first communicator is Bluetooth communication module, and the second communicator is Wi-Fi Direct communication module.

3. The electronic device of claim 2, wherein the controller is further configured to, in response to receiving battery charging information of the paired wireless ultrasound probe through the first communicator, control the display to display the battery charging information of the paired wireless ultrasound probe.

4. The electronic device of claim 2, wherein the controller is configured to control the display to display an ultrasound image corresponding to the ultrasound image data received from the paired wireless ultrasound probe through the second communicator.

5. The electronic device of claim 1, wherein the controller is further configured to, in response to receiving the second user input, control the first communicator or the second communicator to transmit a beam forming control signal for controlling a beam former of the paired wireless ultrasound probe to the paired wireless ultrasound probe.

6. The electronic device of claim 1, wherein the controller is further configured to, in response to receiving a third user input for setting a time gain compensation value, control the first communicator or the second communicator to transmit a control signal for setting the time gain compensation value of the paired wireless ultrasound probe.

7. The electronic device of claim 4, wherein the controller is further configured to, in response to receiving a third user input for freezing the ultrasound image, control the display to pause the ultrasound image being displayed on the display.

8. The electronic device of claim 1, wherein the controller is further configured to, in response to receiving the ID information of the paired wireless ultrasound probe through the first communicator, control the display to display a thumbnail image representing a shape of the paired wireless ultrasound probe.

9. The electronic device of claim 1, wherein the controller is further configured to, in response to receiving an activation completion signal from the paired wireless ultrasound probe, control the display to display a visual indicator indicating that the paired wireless ultrasound probe is being activated.

10. The electronic device of claim 1, further comprising a speaker, wherein the controller is further configured to, in response to the first communicator being paired with the wireless ultrasound probe, control the speaker to output a preset sound.

11. A non-transitory computer-readable medium storing computer-executable instructions when executed by at least one processor of an electronic device, cause the electronic device to perform:
  in response to receiving a first user input for searching a wireless ultrasound probe, controlling a first communicator to output a pairing signal;
  in response to the first communicator being paired with the wireless ultrasound probe and receiving identification (ID) information of the paired wireless ultrasound probe, controlling a display to display the ID information of the paired wireless ultrasound probe; and
  in response to receiving a second user input for activating the paired wireless ultrasound probe, controlling the first communicator or a second communicator to transmit an activation signal to the paired wireless ultrasound probe and controlling the second communicator to receive an ultrasound image data from the paired wireless ultrasound probe.

12. The non-transitory computer-readable medium according to claim 11, wherein the first communicator is Bluetooth communication module, and the second communicator is Wi-Fi Direct communication module.

13. The non-transitory computer-readable medium according to claim 11, wherein when executed by the at least one processor of the electronic device, the instructions cause the electronic device to further perform:
  in response to receiving battery charging information of the paired wireless ultrasound probe through the first communicator, controlling the display to display the battery charging information of the paired wireless ultrasound probe.

14. The non-transitory computer-readable medium according to claim 11, wherein when executed by the at least one processor of the electronic device, the instructions cause the electronic device to further perform:
  controlling the display to display an ultrasound image corresponding to the ultrasound image data received from the paired wireless ultrasound probe through the second communicator.

15. The non-transitory computer-readable medium according to claim 11, wherein when executed by the at least one processor of the electronic device, the instructions cause the electronic device to further perform:
  in response to receiving the second user input, controlling the first communicator or the second communicator to transmit a beam forming control signal for controlling a beam former of the paired wireless ultrasound probe to the paired wireless ultrasound probe.

16. The non-transitory computer-readable medium according to claim 11, wherein when executed by the at least one processor of the electronic device, the instructions cause the electronic device to further perform:
  in response to receiving a third user input for setting a time gain compensation value, controlling the first communicator or the second communicator to transmit a control signal for setting the time gain compensation value of the paired wireless ultrasound probe.

17. The non-transitory computer-readable medium according to claim 14, wherein when executed by the at least one processor of the electronic device, the instructions cause the electronic device to further perform:
  in response to receiving a third user input for freezing the ultrasound image, controlling the display to pause the ultrasound image being displayed on the display.

18. The non-transitory computer-readable medium according to claim 11, wherein when executed by the at least one processor of the electronic device, the instructions cause the electronic device to further perform:
  in response to receiving the ID information of the paired wireless ultrasound probe through the first communicator, controlling the display to display a thumbnail image representing a shape of the paired wireless ultrasound probe.

19. The non-transitory computer-readable medium according to claim 11, wherein when executed by the at least one processor of the electronic device, the instructions cause the electronic device to further perform:
  in response to receiving an activation completion signal from the paired wireless ultrasound probe, controlling the display to display a visual indicator indicating that the paired wireless ultrasound probe is being activated.

20. The non-transitory computer-readable medium according to claim 11, wherein when executed by the at least one processor of the electronic device, the instructions cause the electronic device to further perform:
  in response to the first communicator being paired with the wireless ultrasound probe, controlling a speaker to output a preset sound.

* * * * *